(12) United States Patent
Harris et al.

(10) Patent No.: US 6,602,979 B1
(45) Date of Patent: Aug. 5, 2003

(54) SCREENING ASSAYS FOR COMPOUNDS THAT CAUSE APOPTOSIS

(75) Inventors: Curtis C. Harris, Bethesda, MD (US); Xin Wei Wang, North Potomac, MD (US); Jan H. J. Hoeijmakers, Zevenhuizen (NL)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/359,316

(22) Filed: Dec. 19, 1994

(51) Int. Cl.$^7$ ............................................... C07K 14/00
(52) U.S. Cl. .......................... 530/326; 530/350; 514/13
(58) Field of Search ................................. 530/326, 350; 514/13

(56) References Cited

FOREIGN PATENT DOCUMENTS

| WO | WO 94/08241 | * | 4/1994 |

OTHER PUBLICATIONS

*Proceedings of the American Association for Cancer Research*, vol. 35, Mar. 1994, p. 585.

*Molecular and Cellular Biology*, Hua Xiao, et al. "Binding of Basal Transcription Factor TFIIH to the Acidic Activation Domains of VP16 and p53," vol. 14, No. 10, Oct. 1994, pp. 7013–7024.

*The EMBO Journal*, L. Shaeffer, V. Moncollin, et al., "The ERCC2/DNA repair protein is associated with the class II BTF2/TFIIH transcription factor," vol. 13, No. 10, pp. 2388–2392, 1994.

*Nature*, Imperial Cancer Research Fund, Clare Hall Laboratories,"Localization of p53, retinoblastoma and host replication proteins at sites of viral replication in herpes–infected cells," vol. 349, Jan. 31, 1991, pp. 429–431.

*The New England Journal of Medicine*, C. Harris, M. Hollstein, "Review Articles," Oct. 28, 1993, pp. 1318–1327.

*Proc. Natl. Acad. Sci. USA*, "Hepatitis B virus X protein inhibits p53 sequence–specific DNA binding, transcriptional activity, and association with transcription factor ERCC3," Xin Wei Wang, et al., vol. 91, pp. 2230–2234, Mar. 1994 Medical Sciences.

*Science*, "DNA Repair Helicase: A Component of BTF2 (TFIIH) Basic Transcription Factor," Laurent Schaeffer, et al., vol. 260, Apr. 2, 1993, pp. 58–63.

*The Journal of Biological Chemistry*, "The DNA–dependent ATPase Activity Associated with the Class II Basic Transcription Factor BTF2/TFIIH*," vol. 269, No. 13, Issue of Apr., pp. 9826–9832, 1994.

* cited by examiner

*Primary Examiner*—Brenda Brumback
*Assistant Examiner*—Anish Gupta
(74) *Attorney, Agent, or Firm*—Townsend and Townsend and Crew LLP

(57) ABSTRACT

This invention relates to methods of screening for compounds capable of inducing apoptosis in certain tumor cells. The invention also relates to compounds identified by such methods. In addition, the invention relates to methods for the in vitro diagnosis of Xeroderma pigmentosum and compounds useful in these methods.

2 Claims, 9 Drawing Sheets

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 393 amino acids
      (B) TYPE: amino acid
      (C) STRANDEDNESS: single
      (D) TOPOLOGY: linear (ii) MOLECULE TYPE: protein (ix) FEATURE:
      (A) NAME/KEY: Protein
      (B) LOCATION: 1..393
      (D) OTHER INFORMATION: /note= "human wild-type p53"

(xi) SEQUENCE DESCRIPTION: SEQ ID NO:1:

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Gly Pro Ala Ala Pro
65                  70                  75                  80

Thr Pro Ala Ala Pro Ala Pro Ala Pro Ser Trp Pro Leu Ser Ser Ser
            85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
        130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
```

-continued

```
                225                 230                 235                 240
Ser Cys Met Gly Gly Met Asn Arg Arg Pro Ile Leu Thr Ile Ile Thr
                        245                 250                 255
Leu Glu Asp Ser Ser Gly Asn Leu Leu Gly Arg Asn Ser Phe Glu Val
                260                 265                 270
Arg Val Cys Ala Cys Pro Gly Arg Asp Arg Arg Thr Glu Glu Glu Asn
                275                 280                 285
Leu Arg Lys Lys Gly Glu Pro His His Glu Leu Pro Pro Gly Ser Thr
            290                 295                 300
Lys Arg Ala Leu Pro Asn Asn Thr Ser Ser Ser Pro Gln Pro Lys Lys
305                 310                 315                 320
Lys Pro Leu Asp Gly Glu Tyr Phe Thr Leu Gln Ile Arg Gly Arg Glu
                325                 330                 335
Arg Phe Glu Met Phe Arg Glu Leu Asn Glu Ala Leu Glu Leu Lys Asp
                    340                 345                 350
Ala Gln Ala Gly Lys Glu Pro Gly Gly Ser Arg Ala His Ser Ser His
                355                 360                 365
Leu Lys Ser Lys Lys Gly Gln Ser Thr Ser Arg His Lys Lys Leu Met
        370                 375                 380
Phe Lys Thr Glu Gly Pro Asp Ser Asp
385                 390
```

(2) INFORMATION FOR SEQ ID NO:2:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..21
        (D) OTHER INFORMATION: /note= "peptide # p53cp from amino acid
           residues 367-387 of human wild-type p53 capable of
           inhibiting binding of wild-type p53 to XPB"

(xi) SEQUENCE DESCRIPTION: SEQ ID NO:2:

```
Ser His Leu Lys Ser Lys Lys Gly Gln Ser Thr Ser Arg His Lys Lys
1               5                   10                  15
Leu Met Phe Lys Thr
            20
```

(2) INFORMATION FOR SEQ ID NO:3:

(i) SEQUENCE CHARACTERISTICS:
        (A) LENGTH: 781 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..781
        (D) OTHER INFORMATION: /note= "human xeroderma pigmentosum B
           (XPB) helicase protein"

(xi) SEQUENCE DESCRIPTION: SEQ ID NO:3:

```
Met Gly Lys Arg Asp Arg Ala Asp Arg Asp Lys Lys Lys Ser Arg Lys
1               5                   10                  15
```

-continued

```
Arg His Tyr Glu Asp Glu Asp Glu Asp Ala Pro Gly Asn
         20              25              30

Asp Pro Gln Glu Ala Val Pro Ser Ala Ala Gly Lys Gln Val Asp Glu
         35              40              45

Ser Gly Thr Lys Val Asp Glu Tyr Gly Ala Lys Asp Tyr Arg Leu Gln
         50              55              60

Met Pro Leu Lys Asp Asp His Thr Ser Arg Pro Leu Trp Val Ala Pro
65               70              75              80

Asp Gly His Ile Phe Leu Glu Ala Phe Ser Pro Val Tyr Lys Tyr Ala
                 85              90              95

Gln Asp Phe Leu Val Ala Ile Ala Glu Pro Val Cys Arg Pro Thr His
             100             105             110

Val His Glu Tyr Lys Leu Thr Ala Tyr Ser Leu Tyr Ala Ala Val Ser
             115             120             125

Val Gly Leu Gln Thr Ser Asp Ile Thr Glu Tyr Leu Arg Lys Leu Ser
             130             135             140

Lys Thr Gly Val Pro Asp Gly Ile Met Gln Phe Ile Lys Leu Cys Thr
145              150             155             160

Val Ser Tyr Gly Lys Val Lys Leu Val Leu Lys His Asn Arg Tyr Phe
                 165             170             175

Val Glu Ser Cys His Pro Asp Val Ile Gln His Leu Leu Gln Asp Pro
             180             185             190

Val Ile Arg Glu Cys Arg Leu Arg Asn Ser Gly Glu Ala Thr Glu
             195             200             205

Leu Ile Thr Glu Thr Phe Thr Ser Lys Ser Ala Ile Ser Lys Thr Ala
210              215             220

Glu Ser Ser Gly Gly Pro Ser Thr Ser Arg Val Thr Asp Pro Gln Gly
225              230             235             240

Lys Ser Asp Ile Pro Met Asp Leu Phe Asp Phe Tyr Glu Gln Met Asp
                 245             250             255

Lys Asp Glu Glu Glu Glu Glu Thr Gln Thr Val Ser Phe Glu Val
             260             265             270

Lys Gln Glu Met Ile Glu Glu Leu Gln Lys Arg Cys Ile His Leu Glu
             275             280             285

Tyr Pro Leu Leu Ala Glu Tyr Asp Phe Arg Asn Asp Ser Val Asn Pro
290              295             300

Asp Ile Asn Ile Asp Leu Lys Pro Thr Ala Val Leu Arg Pro Tyr Gln
305              310             315             320

Glu Lys Ser Leu Arg Lys Met Phe Gly Asn Gly Arg Ala Arg Ser Gly
                 325             330             335

Val Ile Val Leu Pro Cys Gly Ala Gly Lys Ser Leu Val Gly Val Thr
             340             345             350

Ala Ala Cys Thr Val Arg Lys Arg Cys Leu Val Leu Gly Asn Ser Ala
             355             360             365

Val Ser Val Glu Gln Trp Lys Ala Gln Phe Lys Met Trp Ser Thr Ile
             370             375             380

Asp Asp Ser Gln Ile Cys Arg Phe Thr Ser Asp Ala Lys Asp Lys Pro
385              390             395             400

Ile Gly Cys Ser Val Ala Ile Ser Thr Tyr Ser Met Leu Gly His Thr
                 405             410             415

Thr Lys Arg Ser Trp Glu Ala Glu Arg Val Met Glu Trp Leu Lys Thr
             420             425             430
```

```
Gln Glu Trp Gly Leu Met Ile Leu Asp Glu Val His Thr Ile Pro Ala
            435                 440                 445

Lys Met Phe Arg Arg Val Leu Thr Ile Val Gln Ala His Cys Lys Leu
            450                 455                 460

Gly Leu Thr Ala Thr Leu Val Arg Glu Asp Asp Lys Ile Val Asp Leu
465                 470                 475                 480

Asn Phe Leu Ile Gly Pro Lys Leu Tyr Glu Ala Asn Trp Met Glu Leu
            485                 490                 495

Gln Asn Asn Gly Tyr Ile Ala Lys Val Gln Cys Ala Glu Val Trp Cys
            500                 505                 510

Pro Met Ser Pro Glu Phe Tyr Arg Glu Tyr Val Ala Ile Lys Thr Lys
            515                 520                 525

Lys Arg Ile Leu Leu Tyr Thr Met Asn Pro Asn Lys Phe Arg Ala Cys
530                 535                 540

Gln Phe Leu Ile Lys Phe His Glu Arg Arg Asn Asp Lys Ile Ile Val
545                 550                 555                 560

Phe Ala Asp Asn Val Phe Ala Leu Lys Glu Tyr Ala Ile Arg Leu Asn
            565                 570                 575

Lys Pro Tyr Ile Tyr Gly Pro Thr Ser Gln Gly Glu Arg Met Gln Ile
            580                 585                 590

Leu Gln Asn Phe Lys His Asn Pro Lys Ile Asn Thr Ile Phe Ile Ser
            595                 600                 605

Lys Val Gly Asp Thr Ser Phe Asp Leu Pro Glu Ala Asn Val Leu Ile
610                 615                 620

Gln Ile Ser Ser His Gly Gly Ser Arg Arg Gln Glu Ala Gln Arg Leu
625                 630                 635                 640

Gly Arg Val Leu Arg Ala Lys Lys Gly Met Val Ala Glu Glu Tyr Asn
            645                 650                 655

Ala Phe Phe Tyr Ser Leu Val Ser Gln Asp Thr Gln Glu Met Ala Tyr
            660                 665                 670

Ser Thr Lys Arg Gln Arg Phe Leu Val Gln Gly Tyr Ser Phe Lys Val
            675                 680                 685

Ile Thr Lys Leu Ala Gly Met Glu Glu Glu Asp Leu Ala Phe Ser Thr
690                 695                 700

Lys Glu Glu Gln Gln Gln Leu Leu Gln Lys Val Leu Ala Ala Thr Asp
705                 710                 715                 720

Leu Asp Ala Glu Glu Glu Val Val Ala Gly Glu Phe Gly Ser Arg Ser
            725                 730                 735

Ser Gln Ala Ser Arg Arg Phe Gly Thr Met Ser Ser Met Ser Gly Ala
            740                 745                 750

Asp Asp Thr Val Tyr Met Glu Tyr His Ser Ser Arg Ser Lys Ala Pro
            755                 760                 765

Ser Lys His Val His Pro Leu Phe Lys Arg Phe Arg Lys
770                 775                 780
```

(2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide (B) LOCATION: 1..15
            (D) OTHER INFORMATION: /note= "peptide # 464 from amino acid
                residues 464-478 of the helicase III region of XPB
                protein capable of inhibiting binding of wild-type p53
                to XPB"

(xi) SEQUENCE DESCRIPTION: SEQ ID NO:4:

Leu Gly Leu Thr Ala Thr Leu Val Arg Glu Asp Asp Lys Ile Val
1               5                   10                  15

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..15
        (D) OTHER INFORMATION: /note= "peptide # 479 from amino acid
                residues 479-493 of XPB protein incapable of inhibiting
                binding of wild-type p53 to XPB"

(xi) SEQUENCE DESCRIPTION: SEQ ID NO:5:

Asp Leu Asn Phe Leu Ile Gly Pro Lys Leu Tyr Glu Ala Asn Trp
1               5                   10                  15

(2) INFORMATION FOR SEQ ID NO:6:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..16
        (D) OTHER INFORMATION: /note= "peptide # 99 irrelevant peptide
                from HBV"

(xi) SEQUENCE DESCRIPTION: SEQ ID NO:6:

Gly Leu Ser Ala Met Ser Thr Thr Asp Leu Glu Ala Tyr Phe Lys Asp
1               5                   10                  15

SCREENING ASSAYS FOR COMPOUNDS THAT CAUSE APOPTOSIS

BACKGROUND OF THE INVENTION

Figure 1A:
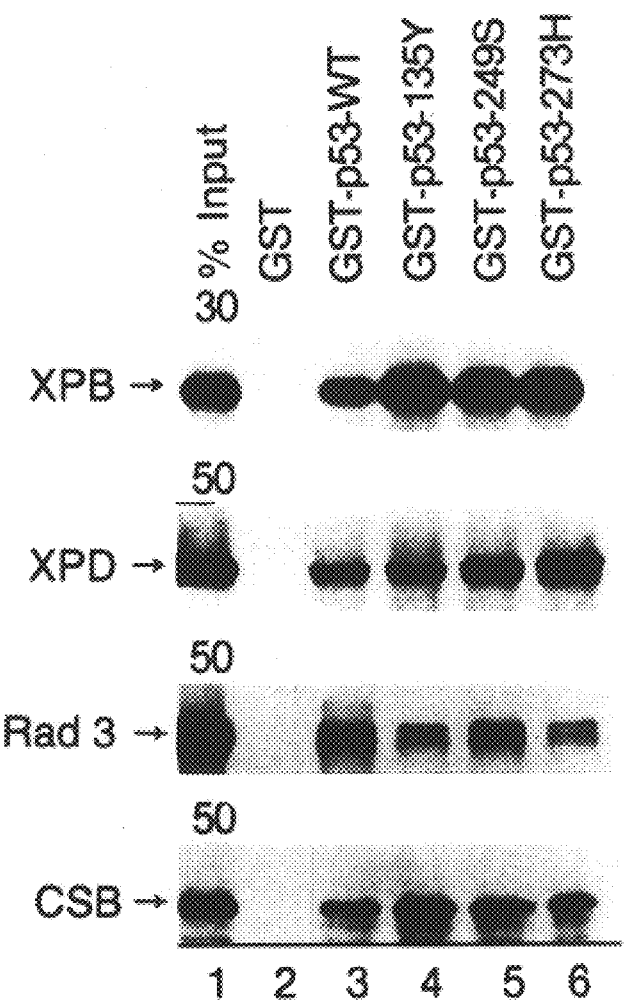

This invention relates to methods of screening for compounds capable of inducing apoptosis in certain tumor cells. The invention also relates to compounds identified by such methods. In addition, the invention relates to methods for the in vitro diagnosis of Xeroderma pigmentosum and compounds useful in these methods.

Certain tumors, benign, premalignant, and malignant, are known to have genetic components etiologically. The gene for the nuclear phosphoprotein, p53, is the most commonly mutated gene identified in human cancers. Missense mutations occur in tumors of the colon, lung, breast, ovary, bladder, and several other organs. When mutant forms of the p53 gene are introduced into primary fibroblasts, these cells are immortalized. The wild type p53 gene can suppress the growth of transformed human cells, but oncogenic forms lose this suppressor function. Thus, the p53 gene has been termed a "tumor suppressor" gene.

If the p53 gene of a tumor cell is of the wild type, its p53 gene product may nevertheless be interfered with functionally. For example, a transforming viral infection of the cell can interfere with the p53 protein product. For instance, certain strains of human papillomavirus (HPV) are transforming and are known to interfere with the p53 protein function because the virus produces a protein, E6, which promotes degradation of the p53 protein.

There is also pharmaceutical interest in p53 because p53 protein is capable of inducing certain tumor cells to undergo apoptosis. In apoptosis, or "programmed cell death" a series of lethal events for the cell appear to be generated directly as a result of transcription of cellular DNA. Thus, apoptosis is a physiologic means for cell death. For example, lymphocytes exposed to glucocorticoids die by apoptosis. Involution of hormone sensitive tissue such as breast and prostate that occurs when the trophic hormone is removed occurs via apoptosis.

In particular, recent studies have indicated that the introduction of wild type (non-mutated) p53 into transformed cell lines that carry a mutant form of p53 induces the cells to undergo apoptosis with disintegration of nuclear DNA. It is believed that p53 may suppress tumor development by inducing apoptosis, thus modulating cell growth.

In addition to p53, there are numerous other genes involved with cell growth. One group of such genes is designated XP because their derangement can result in the disease Xeroderma pigmentosum. Xeroderma pigmentosum is a rare disorder characterized by disfigurement, deranged pigmentation of the skin, scarring and heightened incidence of skin cancers, especially on exposure to sunlight. The disease is inherited as an autosomal recessive trait. Eight genetic forms of the disease are known. Phenotypically these forms vary in their symptoms, signs and severity. Two of the more grave forms are associated with mental deficiencies. These two forms are characterized by mutations in the XPB and XPD genes.

Selection of drugs for potential therapeutic use against tumors is an area of medical research which remains fraught with complications and which often present an array of suboptimal treatment choices. There are currently a multitude of potential compounds available to evaluate. Screening procedures are valuable to limit the bewildering array of drug choices for further testing. Improvements in screening methods or reagents are highly desirable. In addition, there is a need for better diagnosis of XP subtypes. These and other needs are addressed by the present invention.

SUMMARY OF THE INVENTION

The invention provides a method for screening a compound for an ability to induce apoptosis. The method includes providing a first cell containing either a normal or mutant p53 gene. The first cell is responsive to p53. For instance, the first cell is typically capable of undergoing apoptosis after microinjection of a DNA construct expressing wild type p53. The method further includes providing a second cell containing at least one mutant Xeroderma pigmentosum gene such as a mutant XPB gene, or a mutant XPD gene, or both. The second cell is not usually capable of undergoing apoptosis after microinjection of a DNA construct expressing wild type 53. According to a method of the invention, both the first and second cells are contacted with a compound of interest. An example of a compound of interest is any compound one desires to screen for possible use as a chemotherapeutic agent or drug. The method includes detecting whether or not apoptosis of either the first or second cell, or both, occurs after contact of the compound to the cells. A comparison of the observations for apoptosis is made, thereby determining whether the compound can induce apoptosis.

The first and the second cell can be selected from any of a number of cell types including benign, premalignant, and malignant. The first and the second cell can be uninfected or infected. If the latter, the infection can be viral, such as from a papilloma virus. The first and second cell can be selected from any histological or anatomical classification. Typically, the cells are selected from the group consisting of fibroblastic, epithelial, and hematopoietic cells. The cells can be derived from a variety of tissues, including tissue of colon, lung, breast, ovary, cervix, liver, kidney, nervous system, and hematopoietic system. Preferably, the cells are fibroblastic or lymphoblastic cells.

The invention also provides a method of screening for a compound capable of inhibiting the binding of p53 protein to a Xeroderma pigmentosum protein, such as either XPB or XPD proteins or both. This method includes providing a reagent having at least one Xeroderma pigmentosum protein, preferably XPB or XPD, or both. The reagent is contacted with the compound, permitting the compound to compete with wild type p53 protein for a binding site on any or all of the Xeroderma pigmentosum protein(s). Subsequently, any binding of the compound to the protein(s) is detected.

Additionally, this method can include contacting the reagent with wild type p53 protein and detecting a binding of the wild type p53 to at least one of the Xeroderma pigmentosum proteins such as an XPB and\or XPD protein (s). The method can further comprise attaching a label to at least one of the Xeroderma pigmentosum-protein(s) and the p53 protein. The label can be any of a number of detectable labels known in the art. Some examples are an antibody, a radioisotope, and a fluorescent molecule. Conveniently, the reagent has a TFIIH complex containing both XPB and XPD proteins.

The invention also provides a method of screening for a compound capable of inhibiting at least one Xeroderma pigmentosum helicase activity, such as XPB and\or XPD helicase activity. This method includes providing a reagent having at least one Xeroderma pigmentosum protein, contacting the reagent with the compound which permits the compound to bind to the Xeroderma pigmentosum helicase, and determining the helicase activity. Typically, the reagent has a TFIIH complex containing both XPB and XPD proteins.

The invention also provides compositions. In one embodiment, the composition is a compound consisting essentially of the amino acid sequence depicted in Seq. ID No. 2 wherein the compound possesses at least one, usually two, and preferably all three of the following properties: (1) it binds to a binding site on at least one Xeroderma pigmentosum helicase, preferably either the XPB helicase or the XPD helicase or both, (2) it competes with wild type p53 proteins for the binding site, and (3) it inhibits the helicase activity. Conveniently, the compound is a peptide consisting of the sequence depicted in Seq. ID No. 2.

A compound of the invention can be used in a diagnostic method, such as a method of diagnosing a Xeroderma pigmentosum complementation group, preferably group B or D, in an individual. Such a method includes providing a sample cell derived from the individual, contacting the sample cell with a compound of the invention, and detecting whether or not apoptosis of the sample cell occurs, thereby diagnosing whether or not the sample cell contains at least one mutant Xeroderma pigmentosum gene, preferably a mutant XPB gene, a mutant XPD gene, or both.

Another compound of the invention consists essentially of the amino acid sequence depicted in Seq. ID No. 4 wherein the compound possesses at least one, and typically two, of the following properties: (1) it binds to a binding site on wild type p53 protein and (2) it competitively inhibits the binding of wild type p53 protein to wild type XPB protein. Preferably, this compound consists of the amino acid sequence depicted in Seq ID No. 4. Another method of diagnosing a Xeroderma pigmentosum complementation group, such as group B or D, in an individual includes providing a sample cell derived from the individual, contacting the sample cell with a compound of the invention, and detecting whether or not apoptosis of the sample cell occurs, thereby diagnosing whether or not the sample cell contains at least one mutant Xeroderma pigmentosum gene such as a mutant XPB gene, a mutant XPD gene, or both.

BRIEF DESCRIPTIONS OF THE DRAWINGS

Figure 1B:
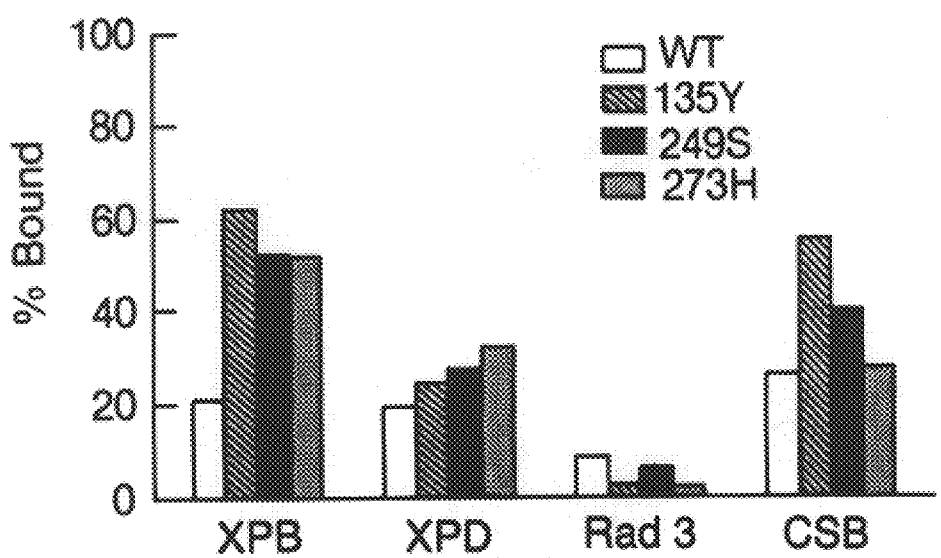

FIGS. 1A and 1B. Human wild-type and mutant p53 protein are able to complex with XPB, XPD, CSR and Rad3 proteins in vitro. A. GSH-beads loaded with either 4 μg of GST (lane 2) or 2 μl of GST-p53-WT (lane 3), GST-p53-135Y (lane 4), GST-p53-249S (lane 5), or GST-p53-273H (lane 6) were mixed with $^{35}$S-labelled, in vitro-translated XPB (5 μl), XPD (5 μl), Rad3 (5 μl), or CSB (15 μl). Proteins which remained bound were analyzed by SDS/PAGE. The authentic XPB, XPD, CSR and Rad3 proteins immunoprecipitated by the specific antibodies were loaded in lane 1 as references. In lane 1, the indicated fraction of XPB, XPD, Rad3, or CSB was immunoprecipitated by anti-XPB polyclonal antibodies (Ab) as a 90 kDa protein, MAb2F6 (anti-XPD monoclonal Ab) as an 80 kDa protein, anti-Rad3 polyclonal Abs as a 85 kDa protein, or anti-CSB polyclonal Abs as a 170 kDa protein, respectively. GST-p53-WT, wild-type p53; GST-p53-135Y, p53 mutated at codon 135 (His→Tyr); GST-p53-249S, p53 mutated at codon 249 (Arg→Ser); GST-p53-273H, p53 mutated at codon 273 (Arg→His). B. The percentage of total protein bound was quantitated by densitometry. The binding between experiments varies by less than 10 percent.

Figure 2A:
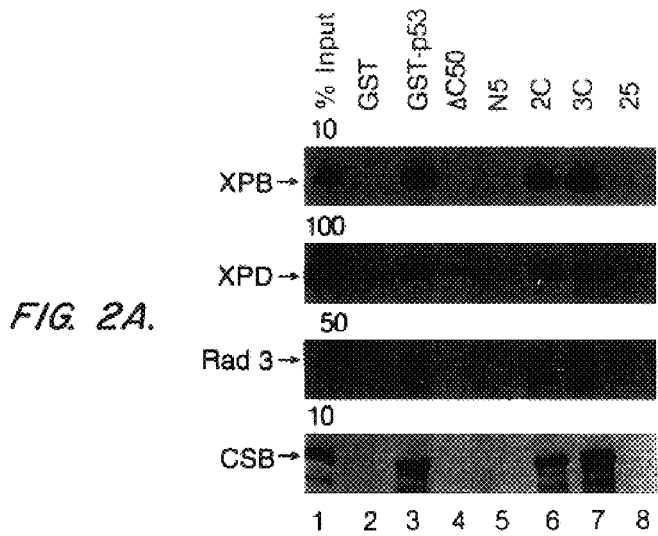
Figure 2B:
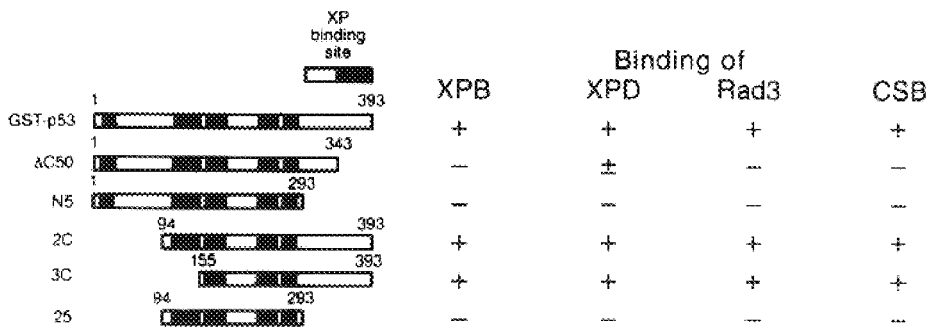

FIGS. 2A and 2B. Carboxyl terminus of p53 is important for association with XPB, XPD, CSR and Rad3 proteins. A. In vitro translated XPB, XPD, CSR and Rad3 proteins were incubated with GSH-beads loaded with either 4 μg of GST (lane 2), or 2 μg each of GST-p53-WT (lane 3), or various GST-p53 deletion mutants (lanes 4–8). In lane 1, the indicated fraction of the XPB, XPD, CSR and Rad3 proteins were immunoprecipitated as in FIG. 1 for the references. B. Schematic representation of wild-type and deletion mutants of human p53 proteins and a summary of their binding properties with in vitro-translated XPB, XPD, CSR and Rad3 proteins. ΔC50, deletion of 50 residues at the C-terminus of p53; N5, deletion of 100 residues at the C-terminus of p53; 2C, deletion of 94 residues at the N-terminus of p53; 3C, deletion of 155 residues at the N-terminus of p53; 25, deletion of both 94 residues at the N-terminus and 100 residues at the C-terminus of p53. The ERCC protein binding site is indicated. The black boxes represent the evolutionarily conserved domains of p53. Degrees of binding: +, binding; ±, reduced binding; −, no binding.

Figure 3C:
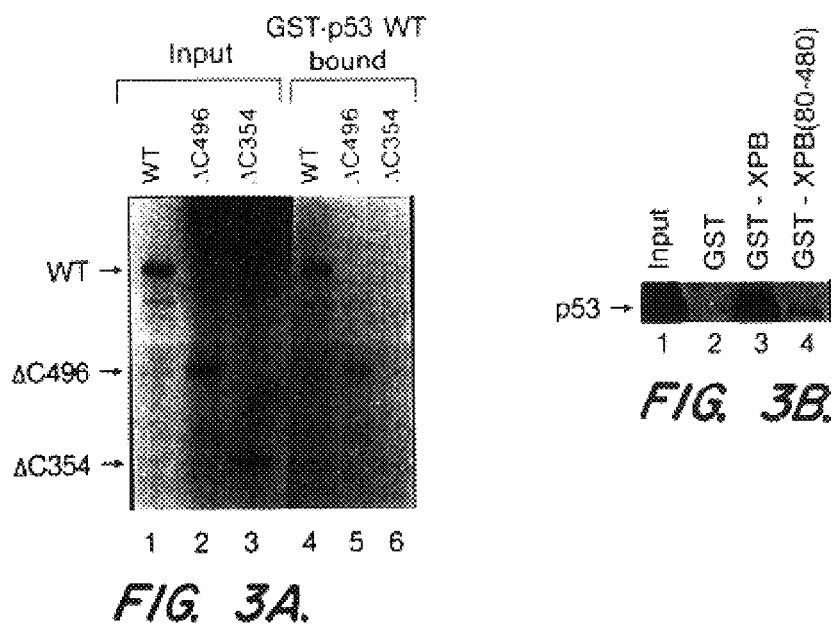

FIGS. 3A, 3B and 3C. p53 binds to XPB helicase motifs Ia, II and III. A. $^{35}$S-labeled, In vitro-translated wild-type XPB (lanes 1 and 4), deletion mutant ΔC496 (lanes 2 and 5), or deletion mutant ΔC354 (lanes 3 and 6) was mixed with GSH-beads loaded with 2 μg of GST-p53-WT and bound proteins were analyzed on SDS/PAGE (lanes 4–6). Twenty percent of the original input was loaded in parallel as the references (lanes 1–3). B. In vitro-translated wild-type p53 protein was mixed with GSH-beads loaded with 4 μg of GST (lane 2), 2 μg of GST-XPB (WT) (lane 3), or 2 μg of GST-XPB (truncated XPB with 80–480 residues) (lane 4). Bound proteins were analyzed on SDS/PAGE. The original input (100%) was included as a reference (lane 1). C. Schematic representation of the full-length or the truncated XPB proteins used in binding assays. Black boxes in the bars are the putative helicase motifs conserved across the helicase superfamily. The small open bar from residues 354 to 496 covers the region which binds p53, with the closed bar in the right side covering motif III representing the higher affinity binding site. Helicase motif 1, residues 337–351; motif Ia, residues 361–374; motif II, residues 434–446; motif III, residues 462–480; motif IV, residues 576–592; motif V, residues 601–621; motif VI, residues 630–649.

Figure 4:
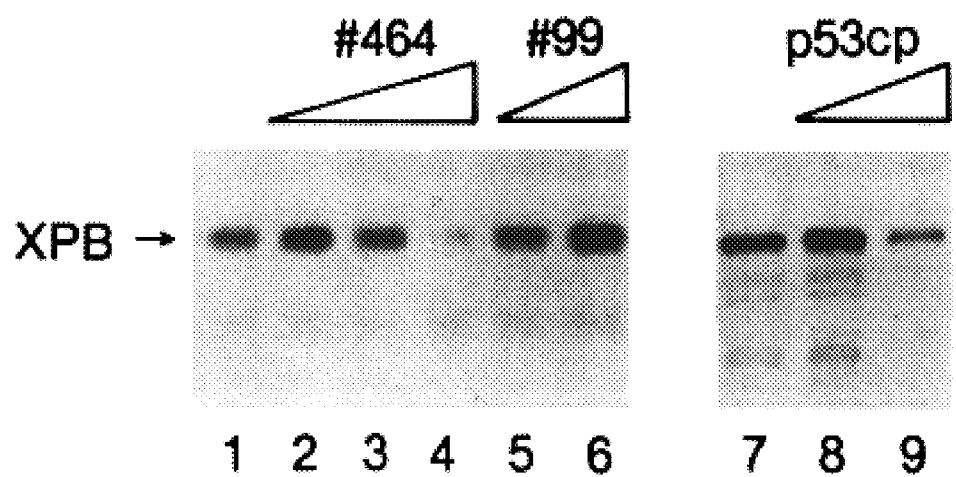

FIG. 4. Peptides corresponding to helicase motif III of XPB and the C-terminus of p53 prevent XPB from binding to GST-p53. Four different synthetic peptides were pre-incubated with 2 μg GST-p53WT for 30 minutes on ice before the addition of $^{35}$S-labeled, in vitro-translated XPB for 60 min at RT. Peptide #464 corresponds to residues 464–478 of XPB (lanes 2–4; 12, 120, and 596 nM), peptide #479 corresponds to residues 479–493 of XPB (lanes 5–7; 12, 116, and 578 nM), peptide #99 corresponds to residues 100–115 of HBX (lanes 8–9; 111 and 554 nM), and peptide #p53cp corresponds to residues 367–387 of p53 (lanes 11–12; 85 and 424 nM).

Figure 5A:
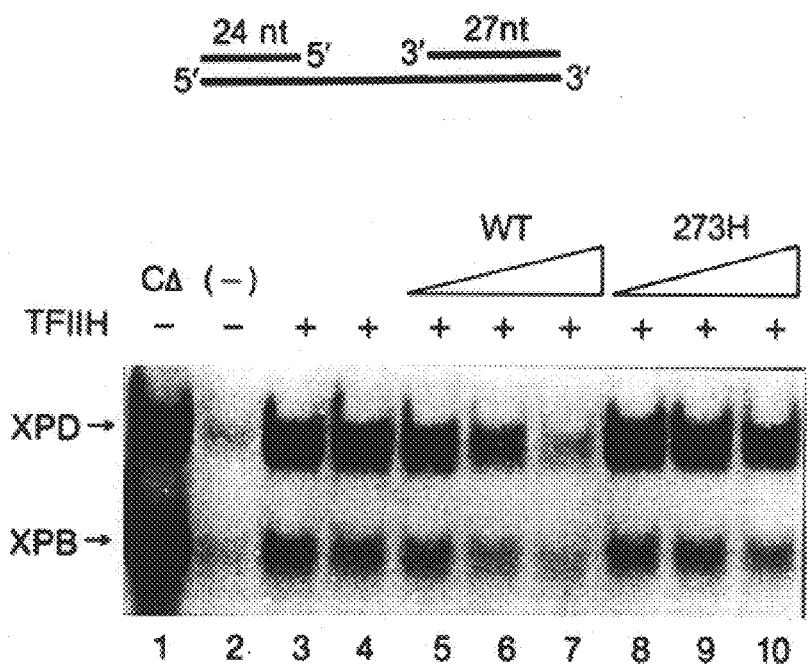
Figure 5B:
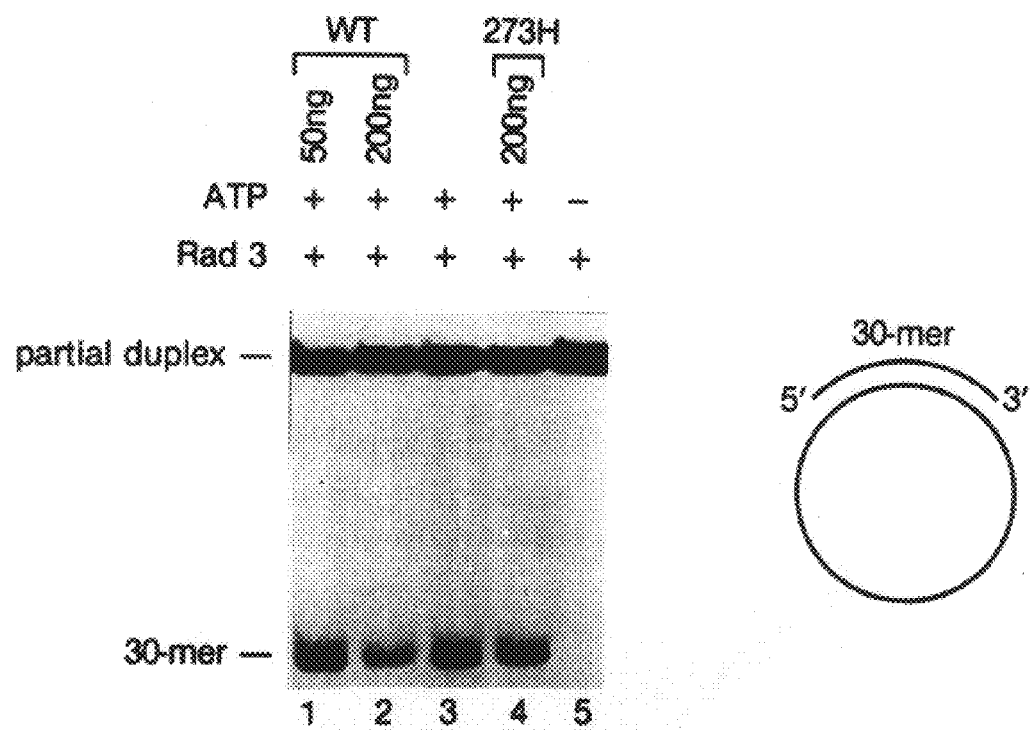
Figure 5C:
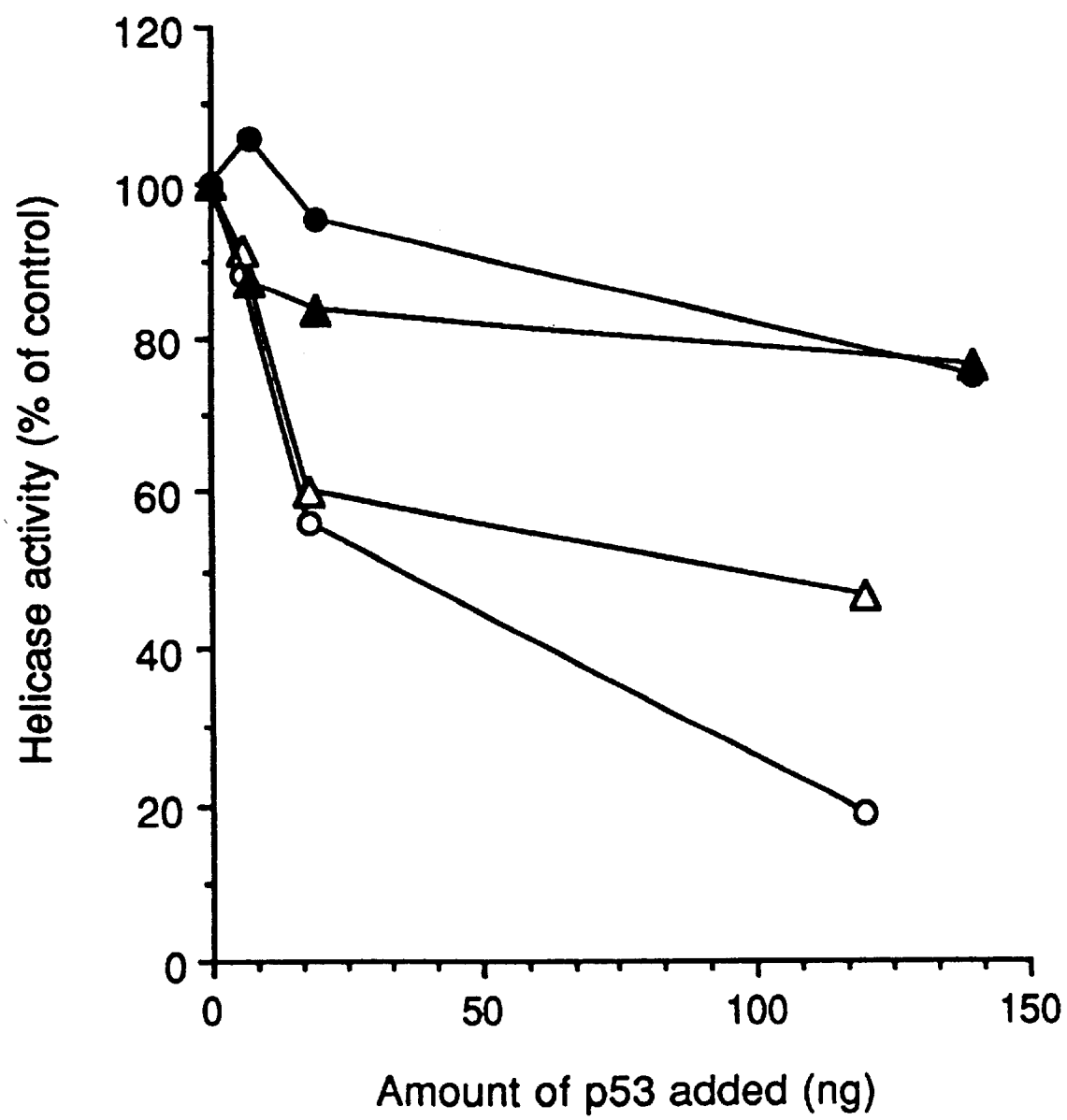

FIGS. 5A, 5B and 5C. Wild-type but not mutant p53 inhibits helicase activity of XPD (Rad3 homologue) and XPB, the major components of BTF2-TFIIH transcription/repair factor. A. Substrate is indicated on the right; the 27 nt (top band) is displaced by XPD (5'→3' helicase) and the 24 nt (bottom band) is displaced by XPB (3'→5' helicase). The $^{32}$P-labeled substrate was incubated with highly purified BTF2-TFIIH (HAP fraction) in the absence (lanes 3 and 4) and in the presence of 6, 18, and 120 ng of baculovirus-produced wild-type p53 (lanes 5–7), or 7, 21, and 140 ng of mutant p53-273H (lanes 8–10). In lane 1, the substrate was heated for 2 min at 100° C. (CΔ) and in lane 2, the substrate was loaded directly (−). Pichia pastoris-produced wild-type p53 produced identical results as in lanes 5–7. B. Effect of p53 on Rad3 helicase activity. DNA helicase activity was measured as described (49) using 90 ng of Rad3 protein in the absence (lane 3) or presence of 50 ng or 200 ng of p53WT (lanes 1 and 2), or 200 ng of mutant p53-273H(B) (lane 4). Helicase activity of 90 ng of Rad3 protein was assayed without 1 mM ATP (lane 5). C. Inhibition of XPD and XPB helicase activities by wild-type p53. The quantitative results obtained from densitometry analysis of the autoradiography shown in FIG. 6A with the amounts of oligomers displayed by XPB and XPD proteins and expressed in the helicase activity as a function of p53 doses. ○, XPD+WT; ∆, XPB+WT; ●, XPD+273H; ▲, XPB+273H.

Figure 6:
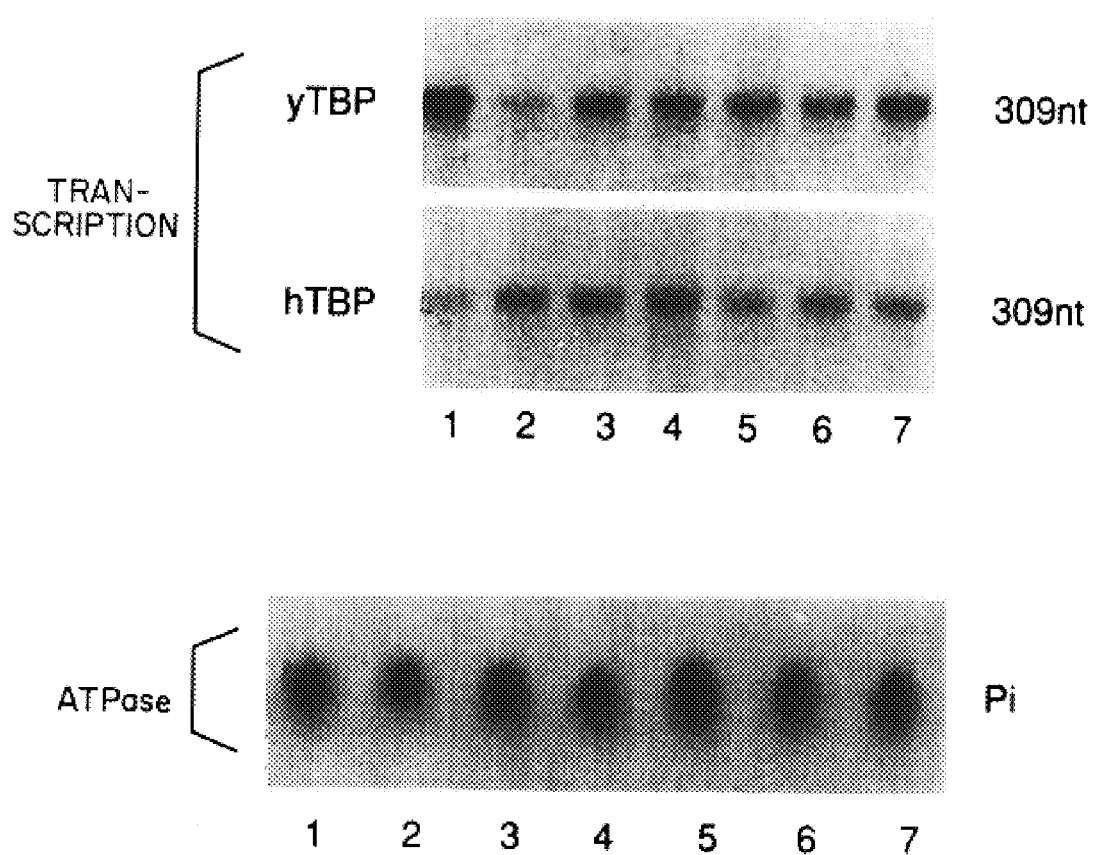

FIG. 6. No inhibition of the BTF2-TFIIH-associated in vitro-transcription of RNA polymerase II or ATPase activity by p53. The purified BTF2-TFIIH was preincubated for 20 minutes at 4° C. without (lane 1) or with 6, 18, and 120 ng of baculovirus- produced wild-type p53 (lanes 2–4), or 7, 21, and 140 ng of mutant p53-273H (lanes 5–7). The transcription reaction was then completed by addition of RNA polymerase II, DNA template, nucleotides and the other basal transcription factors including either yeast TBP (yTBP) or human TFIID (hTBP), and by incubation for 45 min at 25° C. The transcripts were analyzed as described in Example 5, herein. The specific transcript of a 309 nucleotide long (nt) either by yTBP or hTBP is indicated. The ATPase activity of the BTF2-TFIIH with or without p53 was measured as described in Materials and Methods. Pi, inorganic phosphate that is liberated from ATP.

FIGS. 7A, 7B, 7C, 7D, 7E and 7F. Induction of apoptosis by microinjection of the wild-type and various mutant p53 expression vectors in normal primary human fibroblasts. Cells were injected with the expression vectors, including wt (A, B), $143^{ala}$ (C, D), and $249^{ser}$ (E, F), and were incubated for 24 hr prior to fixation. p53 protein was stained with CM-1 antibody (A, C, E). Nuclei were stained by DAPI (B, D, F).

Figure 8:
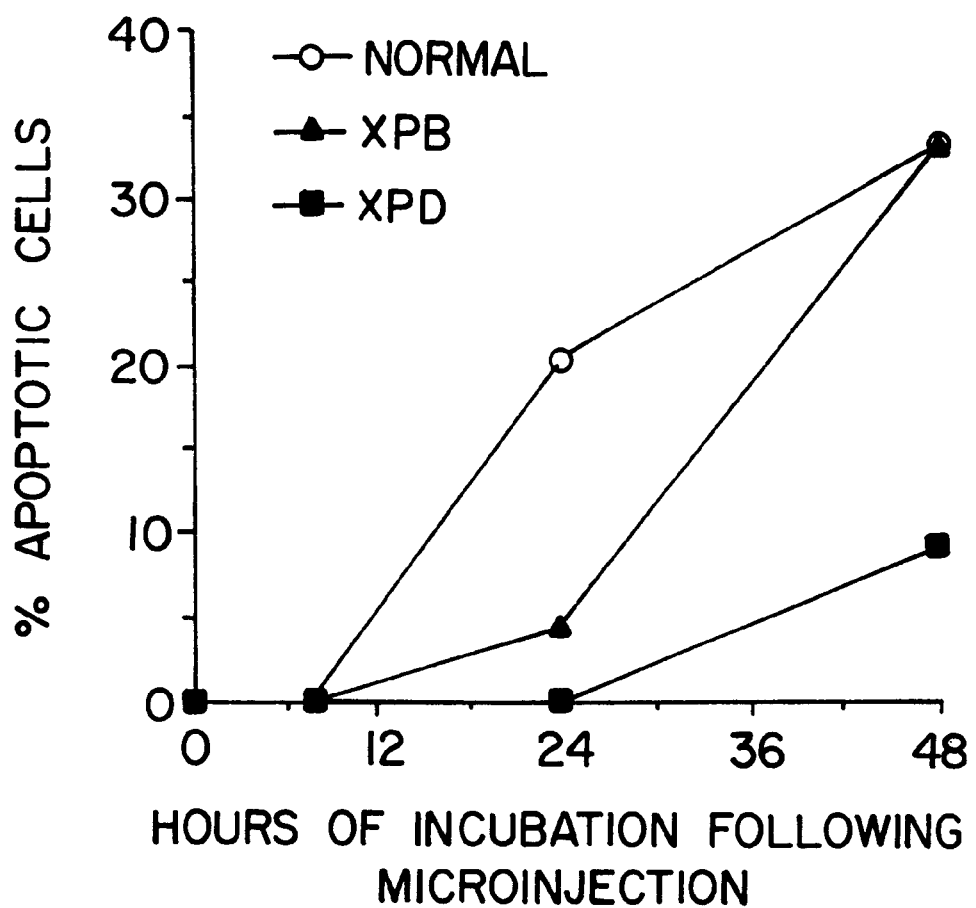

FIG. 8. Differential induction of apoptosis between normal primary human fibroblasts and primary fibroblasts from Xeroderma pigmentosum (XP-B and XP-D) donors following microinjection of the wild-type p53 expression vector.

DETAILED DESCRIPTION

The present invention provides novel methods for screening large numbers of test compounds for those which have the desirable property of inducing apoptosis and which are therefore candidate compounds for treatment of human cancers. There are a variety of agents, including high concentrations of wild type p53 protein, which are capable of inducing certain cells to undergo apoptosis.

High concentrations of wild type (wt) p53 protein can induce apoptosis in a variety of different tumor cells. Tumor cells that are susceptible to induction of apoptosis by wild type p53 proteins include those tumor cells which have a mutant p53 protein. The term "mutant p53 protein", as used herein, refers to mutations in the p53 gene which alter expression of p53 protein in the cell or which result in the production of a p53 protein which is structurally different that wild type p53 protein. Mutant p53 proteins may result from point mutations or deletion mutations in the p53 gene. A variety of different p53 mutations have been identified which are associated with a number of different malignancies. See Hollstein, M. et al. (1991) *Science*, 253:49–53, for a description of p53 mutations found in number of different cancers.

The present invention relies, in part, on the discovery that the p53-dependent apoptosis pathway involves an interaction of p53 protein with XPB and/or XPD proteins. XPB and XPD proteins form part of the RNA polymerase II basal transcription factor, TFIIH. TFIIH contains at least five subunits including XPB, XPD, p62, p44, and p34. XPD and XPB both possess helicase activity and are indispensable for nucleotide excision repair (NER). See Schaeffer, L., et al., *EMBO Journal* (1994) 13:2388–2392 and Schaeffer, L., et al., (1993) *Science* 260:58–63, for a description of XPD and XPB proteins and of TFIIH. As demonstrated in Examples 2–8, herein, p53-dependent apoptosis is mediated, at least in part, by the binding of wild type p53 protein to XPB and XPD proteins. Furthermore, as demonstrated in Example 6, herein, the binding of p53 protein to XPD or XPB proteins results in inhibition of the helicase activity of these proteins.

The present invention encompasses a variety of screening assays for compounds that are capable of inducing apoptosis in tumor cells, and which are based on the interaction between p53 protein and XPB or XPD proteins. The terms "screening assay for apoptosis" or "methods for screening a compound for the ability to induce apoptosis", as used herein, refer to assay methods which are capable of detecting compounds that have the biological activity of inducing apoptosis in certain cells, such as tumor cells having either a wild type or mutant p53 protein.

The screening assays of the invention can be used for screening large numbers of compounds to identify a group of compounds that are candidate compounds for clinical use for treatment of certain cancers. Other compounds that do not have activity in the screening assays can be eliminated from further consideration as candidate compounds. The screening assays therefore have utility in the pharmaceutical industry. In addition to identifying candidate compounds for treatment of malignant diseases, the screening assays are also useful for identifying compounds that can be used in in vitro diagnostics, for example, in the diagnosis of Xeroderma pigmentosum (see below).

There are a variety of different assays for detecting compounds capable of inducing apoptosis that are encompassed by the present invention. For example, there are a number of different screening assays that are based on the binding of wild type p53 protein to XPB and/or XPD proteins. For instance, compounds which inhibit the binding of p53 protein to XPD or XPB protein can be identified in competitive binding assays. Alternatively, the binding of a test compound to XPB or XPD protein can be measured directly, in the presence or absence of wild type p53 protein. This latter type of assay is called a direct binding assay. Both direct binding assays and competitive binding assays can be used in a variety of different formats, similar to the formats used in immunoassays and receptor binding assays. For a description of different formats for binding assays, including competitive binding assays and direct binding assays, see *Basic and Clinical Immunology* 7th Edition (D. Stites and A. Terr ed.) 1991; *Enzyme Immunoassay*, E. T. Maggio, ed., CRC Press, Boca Raton, Fla. (1980); and "Practice and Theory of Enzyme Immunoassays," P. Tijssen, *Laboratory Techniques in Biochemistry and Molecular Biology*, Elsevier Science Publishers B. V. Amsterdam (1985), each of which is incorporated herein by reference.

In competitive binding assays, for example, the sample compound can compete with a labeled analyte for specific binding sites on a binding agent bound to a solid surface. In this type of format, the labeled analyte can be labeled p53 protein and the binding agent can be XPB or XPD protein bound to a solid phase. Alternatively, the labeled analyte can be labeled XPB and/or XPD protein and the binding agent can be a solid phase wild type p53 protein. The concentration of labeled analyte bound to the capture agent is inversely proportional to the ability of a test compound to compete in the binding assay. An example of a competitive binding assay for detecting compounds capable of inhibiting the binding of wild type p53 protein to XPD or XPB protein is described in Example 5, herein. The amount of inhibition of labeled analyte by the test compound depends on the binding assay conditions and on the concentrations of binding agent, labeled analyte, and test compound that are used. Under specified assay conditions, a compound is said to be capable of inhibiting the binding of p53 protein to XPB or XPD protein in a competitive binding assay, if the amount of binding of the labeled analyte to the binding agent is decreased by 10% or more. When a direct binding assay format is used, a test compound is said to inhibit the binding of p53 protein to XPB or XPD protein when the signal measured is twice the background level or higher.

In a competitive binding assay, the sample compound competes with labeled protein for binding to a specific binding agent. As described above, the binding agent may be bound to a solid surface to effect separation of bound labelled protein from the unbound labelled protein. Alternately, the competitive binding assay may be conducted in liquid phase, and any of a variety of techniques known in the art may be used to separate the bound labeled protein from the unbound labeled protein. Following separation, the amount of bound labeled protein is determined. The amount of protein present in the sample is inversely proportional to the amount of labelled protein binding.

Alternatively, a homogenous binding assay may be performed in which a separation step is not needed. In these type of binding assays, the label on the protein is altered by the binding of the protein to its specific binding agent. This alteration in the labelled protein results in a decrease or increase in the signal emitted by label, so that measurement of the label at the end of the binding assay allows for detection or quantitation of the protein.

The binding assay formats described herein employ labeled assay components. The label can be in a variety of forms. The label may be coupled directly or indirectly to the desired component of the assay according to methods well known in the art. A wide variety of labels may be used. The component may be labeled by any one of several methods. Traditionally, a radioactive label incorporating $^3$H, $^{125}$I, $^{35}$S, $^{14}$C, or $^{32}$P is used. Non-radioactive labels include ligands which bind to labeled antibodies, fluorophores, chemiluminescent agents, enzymes, and antibodies which can serve as specific binding pair members for a labelled ligand.

The choice of label depends on sensitivity required, ease of conjugation with the compound, stability requirements, and available instrumentation. For a review of various labelling or signal producing systems which may be used, see U.S. Pat. No. 4,391,904, which is incorporated herein by reference.

The methods of the invention also encompass the use of biologically active fragments of p53 protein or XPB or XPD proteins in the screening assays of the invention. The term "biologically active fragment of wild type p53 protein" refers to fragments of the p53 protein that bind to XPB or XPD proteins. The terms "biologically active fragment of XPB protein" and "biologically active fragment of XPD protein" refer to those fragments of XPB protein and XPD protein respectively that bind to wild type p53 protein.

Methods of production of wild type p53 protein and wild type XPD and XPB proteins, for use in screening assays are known to those of skill in the art. For example, these proteins may be produced as recombinant proteins as described in Example 1, herein.

Another type of screening assay encompassed by the present invention is an assay which identifies compounds capable of inhibiting the helicase activity of XPD or XPB protein. In this type of assay, test compounds are incubated with XPD and/or XPB protein, and the helicase activity is determined. The helicase activity can then be compared to a control which lacks the test compound.

XPD or XPB proteins with helicase activity can be present in the screening assay as individual proteins or as a part of the TFIIH transcription factor complex. TFIIH transcription factor complex can be purified from a variety of different sources by methods known by one of skill in the art. For example, the TFIIH complex can be isolated as described in Example 6, herein. XPD or XPB proteins can also be isolated from natural sources or can be produced as recombinant proteins, for instance, as described in Example 1, herein. See Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987) for a description of techniques useful in the production of recombinant proteins.

Helicase activity can be determined by a variety of assays known to those of skill in the art. For example, helicase activity can be determined as described in Schaeffer, L., et al. (1993) *Science* 260:58–63, 1993; Schaeffer, L., et al. (1994) *EMBO J*. 13:2388–2392; and Roy, R., et al. (1994) *J. Biol. Chem* 269:9826–9832, and in Example 6, herein. When XPB and XPD are present in the TFIIH complex, the helicase activity of XPB, which initiates DNA unwinding in the 3' to 5' direction, and of XPD, which initiates DNA unwinding in the 5' to 3' direction can both be determined as described in Example 6 herein.

A compound capable of inhibiting the helicase activity of XPB or XPD protein is a compound that inhibits at least 10% of the helicase activity of XPB or XPD protein in such an assay. Preferably, the compound inhibits at least 50% of the helicase activity of XPB or XPD protein, and more preferably, the compound inhibits at least 80% of the helicase activity of XPB or XPD protein.

Screening assays utilizing cells expressing mutant XPB and/or mutant XPD proteins are also encompassed by the present invention. These types of screening assays are useful for detecting compounds that are capable of inducing apoptosis by a pathway involving XPD or XPB proteins. At least two different types of cells with differing genetic compositions are used, typically in separate cultures, in this type of assay. One type of cell contains either a wild type or mutant p53 gene, as defined herein, and is capable of undergoing apoptosis when a DNA construct expressing wild type p53 protein is introduced into the cell. This cell also contains XPB and XPD proteins that are functionally wild type. The terms "wild type XPB" and "wild type XPD", as used herein, refer to those proteins that have helicase activity, which are functional when present in normal TFIIH complexes, and that are capable of binding wild type p53 protein.

A second type of cell that is typically tested in a parallel culture in the cellular screening assay is a cell that has a mutant XPB protein and/or a mutant XPD protein, and which is less capable of undergoing apoptosis after introduction of a DNA construct expressing wild type p53. The terms "mutant XPB gene" or "mutant XPB protein" refer to those XPB mutations which confer on a cell the phenotype of having a reduced amount of apoptosis when DNA expressing wild type p53 is introduced into the cell. The terms "mutant XPD gene" or "mutant XPD protein" refer to those XPD mutations which confer on a cell line the phenotype of having a reduced amount of apoptosis when DNA expressing wild type p53 is introduced into the cell line. Cells with mutant XPB and/or mutant XPD proteins may still be able to undergo some degree of apoptosis, but the amount is diminished as compared to control cells.

Cells expressing mutant XPD and/or mutant XPB can be prepared in a variety of ways. For example, such cells can be isolated from patients with genetic disorders affecting the XPD or XPB genes such as Xeroderma pigmentosum. See Example 8, herein, for examples of cells with mutant XPB or mutant XPD genes, which are useful in the screening assays of the invention.

Test compounds are introduced into cell cultures of the cell type more capable of undergoing apoptosis when DNA expressing wild type p53 is put into the cell. Test compounds are also introduced into the cell cultures of a cell type containing mutant XPD and/or mutant XPB. Apoptosis is measured and compounds that are capable of inducing apoptosis it the first cell type, but that are less capable of inducing apoptosis in the second cell type, are selected.

Apoptosis can be measured by a variety of techniques. For example, apoptosis can be measured by determination of cell phenotype. Phenotype refers to how the cell looks, typically microscopically, but gross or macroscopic appearance can be observed. The phenotype changes depending on the growth rate of the cells. For instance, the microscopic morphology of cells that are rapidly dividing and growing is different than that of cells undergoing cell death by apoptosis. Determination of cell phenotype is well within the ability of one with ordinary skill in the art.

There are also a number of biochemical assays that can be used to detect apoptosis, such as "laddering" of the cellular DNA. When testing compounds for the ability to induce apoptosis, cell death (not cytostasis) is an endpoint of compound application to the cell. A classic signature of apoptosis is the cleavage of nuclear DNA into nucleosomal subunits. On gels, this gives rise to the appearance of a ladder as nucleosomal units are sequentially cleaved from the DNA. Observation of a classic DNA ladder is indicative of apoptosis. For example, cells are lysed and the high molecular DNA is removed by centrifugation. The aqueous phase is treated with proteinase K to digest proteins. After a phenol/chloroform extraction, the DNA is precipitated with salt and ethanol. The pellet is dissolved in deionized water and treated with 500 $\mu$g/ml RNase A. The DNA is run on a 2% agarose minigel. Observation for a classic DNA ladders is made. A gel photograph can be taken. Cell death is verified by the demonstration of DNA fragmentation as represented by the ladder configurations on the gel. (See Gavrieli, Y., et al. (1992) *J. Cell Biol.* 119:493). There are also a variety of other assays available for apoptosis such as "TUNEL" assays (see White, E., et al. (1984) *J. Virol.* 52:410). See also Example 7, herein, for a demonstration of the determination of apoptosis.

More than two types of cells can be used in the cellular assay described above. For example, multiple cell lines containing a mutant p53 and/or containing wild type p53 could be used. Multiple cultures of cells with different mutant XPD or mutant XPB protein may also be useful. Furthermore, a variety of different cell lines or cells of different origin can be used. See examples 7 and 8, herein, for a demonstration of the use of human fibroblastic cells and for an example of assay conditions that can be adapted for screening test compounds.

Other types of screening assays based on the interaction of p53 protein with XPB and/or XPD proteins are also encompassed by the invention. In addition, the different types of screening assays described herein may be used in combination with each other to increase the usefulness of the assays. For example, test compounds could first be screened in a binding assay to detect compounds which bind to XPD or XPB. Compounds having binding activity could then be tested in another screening assay, such as the cellular assay described above which uses cells with XPD or XPB mutants.

The present invention also provides compounds that are active in one of the above-described screening assays. These compounds are capable of inducing apoptosis in cells that are susceptible to p53-mediated apoptosis, such as tumor cells. These compounds can also be capable of affecting the interaction of p53 protein with XPB and/or XPD proteins and/or the helicase activity of the XPD or XPB proteins.

The compounds of the invention include peptides from the p53 amino acid sequence that are capable of blocking the binding of p53 protein to XPB protein or the binding of p53 protein to XPD protein. With regard to p53 protein, the full length amino acid sequence of human wild type p53 is shown in Seq. ID No. 1. As described in Example 3, herein, the C-terminal domain of p53 protein contains the binding region for binding to XPB protein. Furthermore, as described in Example herein, peptide #p53cp from the C-terminal region of p53 protein is capable of inhibiting the binding of wild type p53 protein to XPB protein. Peptide #p53cp is depicted in Seq. ID No. 2 and consists of amino acid residues 367–387 of human wild type p53.

The compounds of the invention also include peptides from the XPB and XPD amino acid sequences that are capable of inhibiting the binding of p53 protein to XPB protein or XPD protein, respectively. With regard to XPB protein, the entire amino acid sequence of human XPB protein is shown in Seq. ID No. 3. As described in Example 4, herein, the binding region of XPB protein for p53 protein is located in the helicase motif III region of XPB protein. Furthermore, as described in Example 5 herein, peptide #464 from the helicase III region of XPB protein is capable of inhibiting the binding of wild type p53 protein to XPB protein. Peptide #464 is depicted in Seq. ID No. 4 and consists of amino acid residues 464 to 478 of human wild type p53.

Peptide compositions of the invention include not only the specific peptide sequences shown in Seq. ID Nos. 2 and 4, but also fragments of these two peptides that retain the ability to block the binding of p53 protein to XPB protein. The peptides of Seq. ID No. 2 and Seq. ID No. 4 may also have non-essential moieties attached to the peptides. The term "non-essential moieties", as used herein, refers to those chemical moieties that do not prevent the peptide from inhibiting the binding of p53 protein to XPB protein or to XPD protein. For example, the term "non-essential moieties" includes amino acid sequence extensions at either the amino-terminal or carboxy-terminal end of peptides of Seq. ID Nos. 2 and 4 which do not prevent these peptides from inhibiting the binding to p53 protein to XPB protein or to XPD protein. Examples of such amino acid sequence extensions include the naturally occurring amino acid sequences of p53 protein and XPB protein that are depicted in Seq. ID Nos. 1 and 3, respectively. Preferably, such amino acid extensions are no longer than 100 amino acids in length at either that C-terminal or amino terminal end of peptides of Seq. ID Nos. 2 or 4, and more preferably are no longer than 50 amino acids in length. The ability of any such peptides to block helicase activity of XPB or XPD protein can be determined by the methods described herein.

The peptides of the invention may also have conservative amino acid substitutions from the sequences depicted in Seq. ID Nos. 2 and 4. The substitution of amino acids having similar chemical properties such as charge or polarity are not likely to affect the ability of the peptides to inhibit the binding of p53 protein to XPB protein.

Examples include substitutions of asparagine for glutamine or aspartic acid for glutamic acid.

Peptide compositions of the invention can be produced by a variety of ways known to those of skill in the art. For example, the polypeptides of the invention can be synthetically prepared by wide variety of methods. For instance, polypeptides of relatively short size can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co. (1984). Polypeptides of the invention can also be prepared using recombinant DNA technology. See Sambrook, et al., supra.

Peptides of the invention can be modified according to standard techniques to yield compounds with a variety of desired properties. For instance, the polypeptides can vary from the naturally-occurring sequences described herein at the primary structure level by amino acid insertions, substitutions, deletions, and the like. The amino acid sequence variants can be prepared with various objectives in mind, including facilitating purification and preparation of recombinant polypeptides. Such modifications can also be useful in, for example, modifying plasma half-life, improving therapeutic efficacy, and lessening the severity or occurrence of side effects during therapeutic use.

The invention provides methods of diagnosing Xeroderma pigmentosum complementation group B or D in an individual. A positive diagnosis confirms that the individual has a genetic basis for one or both of the graver forms of the disease. To perform the method, the practitioner selects an individual suspected of having a XP mutation. Testing may include fetal testing in pregnant women. The suspicion can be based on clinical findings, symptoms, family history, or laboratory studies.

A cellular sample is taken from the individual. This sample includes cellular material, and preferably includes whole cells. The sample can employed fresh, but it is usually grown in tissue culture before performing the test. Consequently, the sample can be any cellular material derived from the individual or from a fetal sample. The sample can be taken by any of a number of techniques including tissue scraping, biopsy, washings and aspiration. For example, the clinician can take a mucous membrane scraping, typically buccal or cervical; a skin biopsy; or a bone marrow aspiration. Preferably, skin fibroblasts or blood lymphocytes are used.

The sample cell is contacted with a compound of the invention, preferably the peptide of Seq. ID No. 2 or Seq. ID No.4. Contact is preferably made by applying the compound directly in an aqueous solution to the sample in a tissue growth medium. Alternatively, a DNA construct expressing the compound could be prepared and microinjected into the cell(s).

After a sufficient time period, the practitioner observes whether or not apoptosis of the material derived from the cellular sample occurs. Detection of apoptosis can be accomplished by any of a number of means such as those discussed herein. For example, preparation and staining for DNA ladders is done, although other methods, direct and indirect, are available. If apoptosis is detected, then the practitioner diagnoses that the sample cell contains at least one mutant Xeroderma pigmentosum gene, either a mutant XPB gene or a mutant XPD gene, or both.

The foregoing description and the following examples are offered primarily for purposes of illustration. It will be readily apparent to those skilled in the art that the operating conditions, materials, procedural steps and other parameters of the system described herein may be further modified or substituted in various ways without departing from the spirit and scope of the invention. Thus the invention is not limited by the description and examples, but rather by the appended claims.

EXAMPLES

Example 1

Production of Recombinant Proteins

A. Production of Expression Plasmids

GST-p53-WT encodes glutathione S-transferase (GST) fused to human wild type p53. GST-p53-135Y, -249S, and -273H encode GST fused to p53 mutated at codon 135 (his→tyr), 249 (arg→ser), and 273 (arg→his), respectively. The production of these constructs are described in Wang, X. W., et al. (1994) *Proc. Natl. Acad. Sci. USA* 91:2230–2234. ΔC50 encodes a GST-p53 fusion protein with a deletion of the last 50 amino acids. ΔC50 was made by PCR amplification of the first 1,028 nucleotides (nt) of p53 from pC53-SN, (obtained from of Bert Vogelstein, Johns Hopkins University. Korn, S. E., Pietenpol, J. A., Thiragalingam, S., Seymour, A., Kirzler, K. W. and Vogelstein, B., *Science* 256:827–830, 1992. The PCR product was inserted into the BamHI site of pGEX-2T (Pharmacia LKB, Uppsala, Sweden). Plasmids N5, 2C, 3C, and 25 as described in Ruppert, J. M. and Stillman, B., (1993) *Mol. Cell Biol.* 13:3811–3820 encode GST fused to amino acids 1–293, 94–393, 155–393, and 94–293 of p53, respectively. These plasmids were obtained from Bruce Spillman at Cold Spring Harbor Laboratory. Plasmid pZAP10, encoding a XPB cDNA under the control of bacterial T7 promoter, was used for in vitro translation of full length XPB protein, and was linearized with PstI and SphI for in vitro translation of ΔC496 and ΔC354.

pGEM3zf(+)T7XPD was used for in vitro translation of XPD protein with a T7 promoter. pGEM4z-SP6ccaccRAD3 was used for in vitro translation of Rad3 protein with a SP6 promoter. pcBLsSE6 was used for in vitro translation of CSB with a T7 promoter. GST-XPB-80/480 encodes GST fused to amino acids 80 to 480 of XPB. GST-XPB, encoding GST fused to full length XPB, was constructed by PCR amplification of the XPB coding region in pZAP10 and insertion into the BamHI and EcoRI sites of pGEX-2T. pSelectp53 was used for in vitro-translation of human wild-type p53 protein as described in Wang, X. W., et al. (1994) *Proc. Natl. Acad. Sci. USA* 91:2230–2234. pPOLY(A)-luc (SP6) (Promega, Madison, Wis., USA) was used for in vitro translation of luciferase. pcref, constructed by Chris Chay in the Laboratory of Human Carcinogenesis, National Cancer Institute, Bethesda, Md. 20892, was used for in vitro translation of REF1.

B. Expression and Purification of Recombinant Proteins

GST fusion proteins were produced in *Escherichia coli* and purified on glutathione-Sepharose 4B beads (GSH-beads) according to the manufacturers' directions (Pharmacia LKB). The purified fusion proteins immobilized on the surface of GSH-beads were stored at 4° C. in phosphate-buffered saline, pH7.4, containing 1% Triton X-100 for up to two months. Protein concentrations were determined by Coomassie blue staining of SDS/PAGE and comparison to molecular weight standards (BioRad, Hercules, Calif., USA) run on the same gel. Highly purified baculovirus-produced p53-WT and p53-273H proteins were kindly provided by Carol Prives (Columbia University), Wang E. H, Friedman, P. N. and Prives, C., *Cell* 57:379–392, 1989, and were proved to be the biologically active forms. To label the in vitro translated proteins, the corresponding plasmids were used in a one-step in vitro transcription and translation system (Promega) at room temperature (RT) for 90 min in the presence of [$^{35}$S]Cysteine (Dupont, Boston, Mass., USA). In vitro-translated proteins were freshly prepared each time, prior to use.

Example 2

Binding of Wild Type and Mutant p53 with Nucleotide Excision Repair (NER) Proteins A. Binding of Wild Type P53

In order to demonstrate that wild type p53 interacts with NER proteins, human wild type p53 protein was tagged at the N-terminus with glutathione S-transferase (GST) as described in Example 1. p53 protein was incubated with in vitro translated $^{35}$S-labeled XPD, Rad3, XPB, or CSB protein, which were also produced as described in Example 1. The binding assays were done in 500 μl IP buffer (50 mM Tris-HCl, pH8.0/120 mM NaCl/0.5% Nonidet P-40) containing the $^{35}$S-labeled, in vitro translated proteins and GST fusion proteins loaded on GSH-beads at RT for 60 min. After washing five times with IP buffer, the bound proteins were released by boiling the beads in Laemmli buffer for 5 min, separated by SDS-PAGE, and visualized by flurography, as described in Wang, X. W., et al. (1994) *Proc. Natl. Acad. Sci., USA* 91:2230–2234. The results are shown in FIG. 1. XPD, XPB and CSB bind to GST-p53-WT with a relatively higher affinity (about 20% of input) than Rad3 (about 10% of input) (see FIG. 1A, comparing lane 1 with 3). GST alone did not interact with any of the four proteins (lane 2, FIG. 1). In vitro-translated REF1, a nuclear factor involved in DNA repair and a redox pathway, as well as in vitro-translated luciferase and other non-relevant proteins present in the translation mix, did not bind to either GST-p53-WT or GST-XPB. Binding was not mediated through single stranded (ss) DNA and RNA, as was demonstrated by the treatment of in vitro-translated products with DNAse and RNAse prior to binding.

B. Binding of Mutant p53 Proteins

In order to demonstrate the binding of several mutant p53 proteins to NER proteins, equal amounts of GST-tagged p53 mutants, (135Y, 249S, 273H) were tested for binding to the in vitro-translated XPD, XPB, CSB and Rad3 proteins used above. The mutant p53 proteins were produced as described in Example 1 and were tested for binding to NER proteins in the same manner as was wild type p53. The results are shown in FIG. 1. All the mutants tested had similar or increased binding to the human proteins but decreased binding to yeast Rad3, as compared to GST-p53-WT (see FIG. 1A, comparing lane 3 with lanes 4, 5, and 6). While not wishing to be bound by theory, this opens the possibility that mutant p53 may exert a dominant negative effect by binding to and sequestering the cellular targets of wild-type p53. The p53-135Y mutant, which has diminished binding to hepatitis B virus X protein and papillomavirus E6 protein, binds to XPD, XPB, Rad3 and CSB. HBX has also been shown to inhibit p53 binding to XPB presumably by binding to the same site of p53 that interacts with XPB, since HBX did not bind to XPB in vitro (see Wang, X. W., et al. (1994) *Proc. Natl. Acad. Sci., USA* 91:2230–2234.)

Example 3

Binding of Mutant p53 Proteins with C-terminal Deletions to Nucleotide Excision Repair (NER) Proteins Defining the protein domains required for various interactions can provide clues to the significance of the interaction, especially if the domains are functionally important. The importance of the C-terminal domain of p53 for binding to NER proteins was demonstrated by the use of mutant p53 proteins with C-terminal deletions that were tagged with GST. The deletion mutant p53-GST fusion proteins were prepared as described in Example 1 herein, and binding studies to NER proteins were performed as described in Example 2 herein. The results are shown in FIG. 2.

Deletion of the 50 C-terminal amino acids abolished binding of XPB, Rad3 or CSB, and reduced binding of XPD, while deletion of up to 155 N-terminal amino acids had no detectable effect (see FIG. 2). XPD binding diminished with deletion of the 100 C-terminal amino acids (FIG. 2A, comparing lane 5 to lane 3). The effect of C-terminal deletions of various length on p53 binding to NER proteins is summarized in FIG. 2(C). The results suggest that the C-terminal region of p53 is involved the binding of p53 to XPD and XPB.

Example 4

Binding of XPB Proteins with Deletion Mutations to Wild Type p53

Figure 3C:
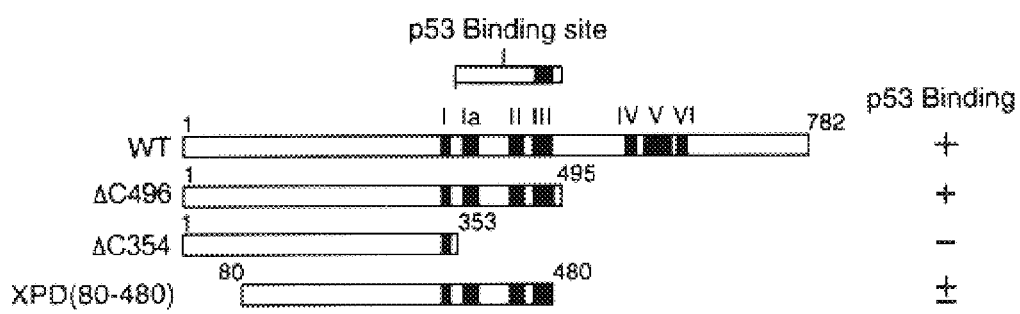

XPB contains 7 putative helicase motifs (FIG. 3C, black bars) which are conserved among the helicase superfamily and are indispensable for NER activity. In order to demonstrate that p53 interacts with a helicase domain of XPB, three C-terminal deletion mutants of XPB were translated in vitro and assayed for binding to GST-p53-WT. The XPB mutants were produced as described in Example 1, herein, and the binding studies with wild type p53 were carried out as described in Example 2, herein. The results are shown in FIG. 3.

A deletion mutant terminating at residue 496 (mutant ΔC496, i.e., deletion of helicase motifs IV, V and VI) did not alter the binding to wild type p53 (see FIG. 3A, comparing lane 5 to lane 2). However, further deletion to residue 354 (mutant ΔC354, i.e., deletion of helicase motifs Ia, II, III, IV, V and VI) completely abolished the binding to p53 (see FIG. 3A, comparing lane 6 to lane 3). While full-length GST-XPB fusion protein effectively binds in vitro-translated human wild-type p53 (FIG. 3B, compare lane 3 to lane 1), an XPB fragment containing residues 80–480 tagged with GST showed significantly less binding (FIG. 3B, compare lane 4 to lane 3). Similar patterns were observed when GST-p53-135Y, 249S or 273H mutants were used (data not shown). These results indicate that p53 binds to XPB at a region within or near helicase motif III (residues 462–495).

We used the Chou-Fasman and the Robson-Garnier methods (see Chou, P. Y. and Fasman, G. D., (1974) *Biochemistry*

13:222–245, and Garnier, J., et al. (1978) *J. Mol. Biol.* 120:97–120) to predict possible secondary structures for the two interacting regions of p53 and XPB. The conserved helicase motif III consists of a 3–6 residue turn containing 1–3 acidic (negatively charged) residues, which are likely to be exposed on the protein's surface, and which are separated by two α-helices or β-sheets, depending on the particular member of the superfamily. Sequence analysis of the C-terminal p53 domain reveals that it contains a stretch of basic (positively charged) amino acids (residues 367 to 387) which are evolutionarily conserved from Xenopus to human. This region is likely to form an α-helix with all the positively charged residues facing one side. While not wishing to be bound by theory, we hypothesize that this positively charged α-helical domain of p53 may be in direct contact with the negatively charged turn of helicase motif III in XPB.

The p53 tumor suppressor gene product selectively binds to several helicase proteins which are part of a transcription/repair complex, BTF2-TFIIH. This conclusion is based on the observations that: a) GST-p53-WT binds specifically to in vitro-translated XPD, XPB, CSB, or Rad3 proteins, but not to truncated XPB protein with helicase motifs Ia, II, III deleted, and not to in vitro-translated luciferase and REFI proteins or to other non-relevant peptides present in the translation mix; b) full length GST-YPB binds to in vitro-translated p53 but a GST-XPB fragment (residues 80–480) has reduced binding activity; c) GST-p53-135Y mutant protein binds to the tested ERCC proteins although it has diminished binding to in vitro-translated hepatitis B viral X protein and human papillomavirus E6 protein; and d) GST-p53 deletion mutants have diverse binding activity to the XPD, XPB, CSB proteins. While not wishing to be bound by theory, the fact that p53 binds to many helicases which are involved in both RNA polymerase II transcription and NER suggests that p53 may play an important role in the maintenance of genomic integrity not only by controlling the cell cycle, but also by direct participation in the nucleotide extension repair (NER) pathway.

Example 5

Inhibition of Binding of Wild Type 53 to XPB by p53 and XPB Peptides

The helicase motif III in XPB and the C-terminal region of p53 are both important regions that are involved in the binding of p53 to XPB. We therefore used peptides corresponding either to helicase motif III or to the p53 C-terminal domain to competitively inhibit the binding of p53 to XPB. For these competitive binding studies, binding assays were done by preincubation of GST-p53-WT containing beads with various concentrations of peptides for 30 min on ice followed by addition of in vitro-translated proteins. Incubation conditions for the binding assays and analysis of binding was then carried out as described in Example 2 herein. The results are shown in FIG. 4.

Peptide #464 (residues 464 to 478 of XPB), depicted in Seq. ID No. 4, efficiently competed in vitro-translated XPB from GST-p53 (see FIG. 4, comparing lane 4 to lane 1), while peptide #479 (residues 479 to 493 of XPB), depicted in Seq. ID No. 5, and a non relevant peptide #99 (from HBV), depicted in Seq. ID No. 6, failed to do so. Instead, the latter two peptides served to enhance binding (see FIG. 4, comparing lanes 6,7 and 9 to lane 1). We have no explanation why peptide #479 and #99 enhance binding. As expected, peptide #p53cp (residues 367 to 387 of p53), and depicted in Seq. ID No. 2, also competed in vitro translated XPB from GST-p53 (see FIG. 4A, comparing lane 12 to lane 10). We conclude that motif III of XPB directly interacts with the p53 C-terminal domain. However, these peptides did not compete XPD, CSB and Rad3 from GST-p53 (data not shown). This may reflect a heterogeneity among these helicases involved in the interaction. A more precise molecular genetic approach, such as site-directed mutagenesis, will be needed to further characterize these interactions. In addition, peptide #464 did not inhibit XPB from binding to mutant p53 (data not shown), suggesting that mutant p53 may require an additional binding site for XPB.

Example 6

Inhibition of the Helicase Activity of BTF2-TFIIH by Wild Type p53

We demonstrate below that p53 binding alters the helicase activity of XPD and XPB within the functional BTF2-TFIIH complex and the Rad3 protein. Native BTF2-TFIIH was purified from a HeLa cell nuclear extract as described by Schaeffer, L., et al. (1993) *Science* 260:58–63. The helicase and ATPase assays of BTF2-TFIIH are essential as described in Schaeffer, L., et al. (1993) *Science* 260:58–63, 1993; Schaeffer, L., et al. (1994) *EMBO J.* 13:2388–2392; and Roy, R., et al. (1994) *J. Biol. Chem* 269:9826–9832. Purification of Rad3 as well as its ATPase and helicase assays were as described elsewhere in Naegeli, H. et al. (1992) *J. Biol. Chem* 267:392–398. The BTF2-TFIIH complex was shown to be transcriptionally active and contained both ATP-dependent 5'→3' (contributed by XPD) and 3'→5' (contributed by XPB) helicase activities by using the helicase assays described above. This system of assays allows us to simultaneously assay and distinguish between XPD and XPB helicase activity within the native BTF2-TFIIH complex. (see FIG. 5).

A highly purified human wild-type recombinant p53 protein produced from baculovirus effectively was shown to inhibit intrinsic BTF2-TFIIH helicase activity in a dose-dependent manner (FIG. 5A, both orientations, compare lanes 5–7 to lanes 3 and 4; FIG. 5C). XPD was inhibited to a greater degree than XPB (FIG. 5C). No inhibition was observed with the addition of mutant p53-273H (FIG. 5A, comparing lanes 9–10 to lanes 3 and 4; FIG. 5C), even though it binds to XPD and XPB proteins (see FIG. 1). Thus, wild-type p53 was demonstrated to inhibit helicase activity XPD and XPB, while mutant p53 did not inhibit this activity.

It has been reported that wild-type p53 binds preferentially to the ends of single-stranded (SS) DNA or RNA in vitro, and catalyzes DNA or RNA strand reassociation. While not wishing to be bound by theory, inhibition of the helicase activity of BTF2-TFIIH and Rad3 in our system does not appear to be due to the strand annealing activity of p53, but rather due to direct interaction with these factors. This conclusion is based on the following data. First, p53 selectively binds to XPD and XPB, which are the major components of the 5'→3' and 3'→5' DNA helicase activities of BTF2-TFIIH. Second, p53 at a similar concentration used in the BTF2-TFIIH helicase assay inhibits Rad3 helicase activity to a similar extent with a substrate containing a circular ss DNA that does not preferentially bind to p53. Third, inhibition of the BTF2-TFIIH helicase activity is not uniform for XPD and XPB, i.e., XPD is affected to a greater degree than XPB (see FIG. 5C).

Example 7

Induction of Apoptosis in Normal Human Fibroblasts by p53

Figure 7:
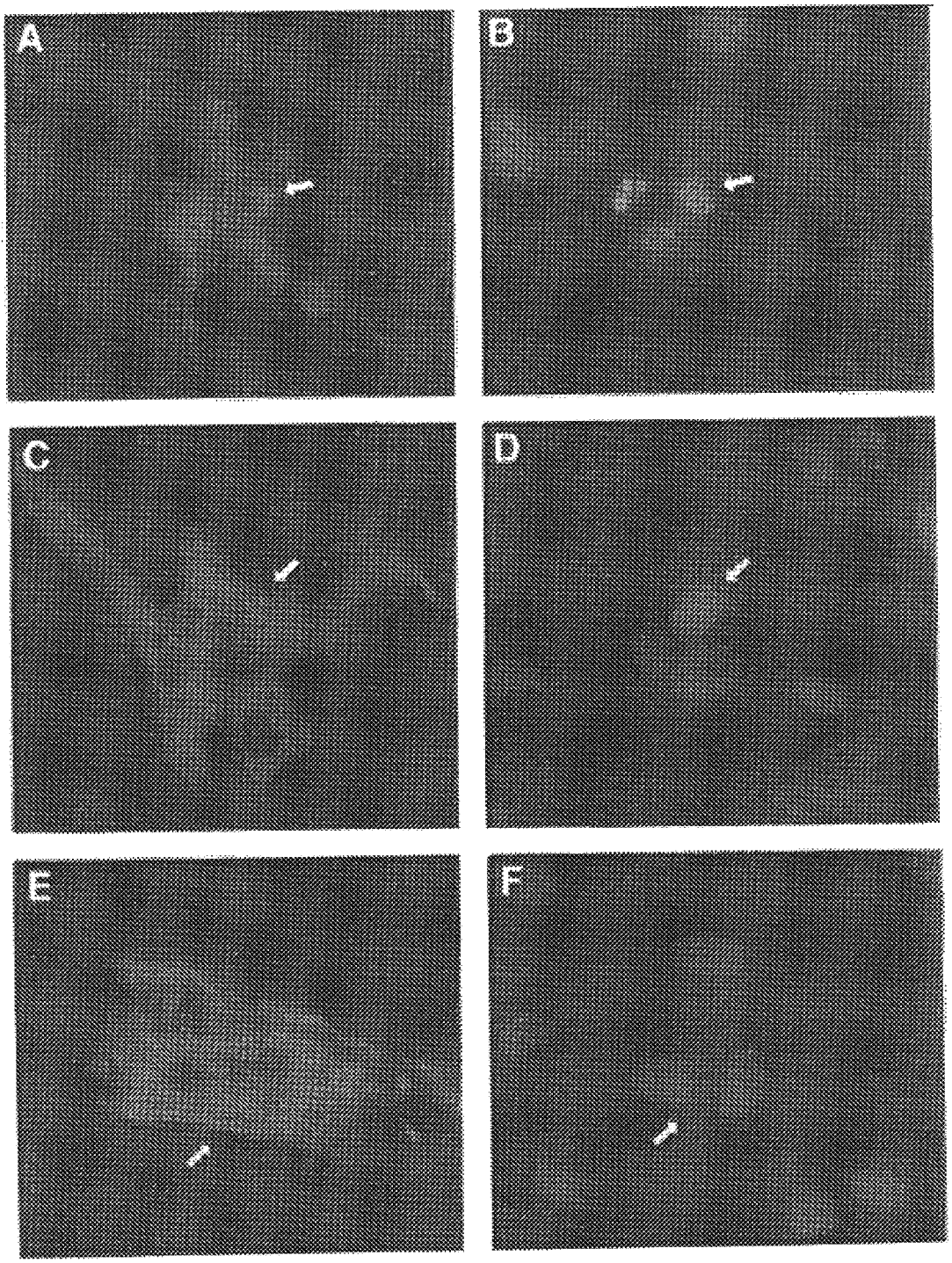

In order to demonstrate that increased levels of wt p53 are sufficient to induce apoptosis in normal human fibroblasts, we used a microinjection technique to deliver an expression vector encoding wt p53 under the control of the cytomegalovirus early promoter (CMV) into the nuclei of homopolykaryons of fused normal human primary fibroblasts (C5RO). These homopolykaryons have lost proliferation potential and are arrested primarily in G1 of the cell cycle (see Vermeulen, W., et al. (1994) *Am. J. Hum. Genet.* 54:191). Cell strains, culture conditions, cell hybridization and microinjection were as described in Vermeulen, W., et al. (1994) *Am. J. Hum. Genet.* 54:191. Primary human fibroblasts were grown in Ham's F10 medium supplemented with 10% FBS and fused with β-propiolactone-inactivated Sendai virus. Fused cells were seeded onto coverslip and incubated for additional 2–3 days prior to injection. Plasmid cDNA in a concentration of 100–200 µg/ml suspended in PBS was injected into one of the nuclei of homopolykaryons by using a glass microcapillary. For each experiment, at least 50 homopolykaryons were injected. Following incubation, cells were fixed with 2% paraformaldehyde (in PBS) followed by methanol treatment. p53 was visualized by staining cells with CM-1 antibody (Signet Labs, Dedham, Mass. U.S.A.) followed by fluorescein conjugated anti-rabbit lgG (Vector Labs, Burlingame, Calif., USA). Nuclei were stained with 4',6-diamidino-2-phenylindole (DAPI). The results are shown in FIG. 7 and summarized in Table 1.

High levels of wt p53 were observed 24 hrs following injection, predominantly in the nucleus or in both the nucleus and cytoplasm (FIG. 1A, Table 1) and 20% of the cells displayed the typical characteristic features of apoptosis, including chromatin condensation, nuclear fragmentation and apoptotic bodies (FIG. 1B and data not shown). This percentage is an underestimate since apoptotic bodies staining positive for p53 were visible when most cells and debris were detached from the plates (data not shown), and these residual cells were not scored.

TABLE 1

Induction of apoptosis by wild-type or mutant p53 in normal primary human fibroblasts

| Expression Vectors | % apoptotic cells$^a$ (n)$^b$ | p53 localization (% cells) | | |
|---|---|---|---|---|
| | | nuclei | cytoplasmic | both |
| WT p53 | 20(152) | 28 | 0 | 72 |
| 143$^{ala}$ | 0(18) | 11 | 6 | 83 |
| 175$^{his}$ | 0(38) | 26 | 24 | 50 |
| 248$^{trp}$ | 0(36) | 44 | 8 | 48 |
| 249$^{ser}$ | 0(34) | 6 | 77 | 17 |
| 273$^{his}$ | 7(30) | 27 | 0 | 73 |
| WT + 143$^{ala}$ | 0(16) | 13 | 6 | 81 |
| WT + 175$^{his}$ | 0(17) | 12 | 47 | 41 |
| WT + 248$^{trp}$ | 0(24) | 63 | 16 | 21 |
| WT + 249$^{ser}$ | 0(20) | 45 | 20 | 35 |
| WT + 273$^{his}$ | 0(15) | 33 | 33 | 34 |

$^a$Cells with the condensed and fragmented nuclei as well as the crater-like body characteristic of cells going under apoptosis.
$^b$Number of p53 positive cells following microinjection of the p53 expression vectors.

To demonstrate that induction of apoptosis was due specifically to an intrinsic activity of wt p53 and not the result of nonspecific protein overproduction, p53 mutants, 143$^{ala}$, 175$^{his}$, 248$^{trp}$, 249$^{ser}$ and 273$^{his}$, were microinjected in the same expression system. These p53 mutants all lack the sequence-specific transcriptional activation activity that is associated with growth suppression. All mutants were expressed at similar or higher levels of protein when compared to the wt p53 (FIGS. 1C, 1E and unpublished data). The p53 mutants showed similar subcellular localization with both nuclear and cytoplasmic staining, except for 249$^{ser}$, that accumulated predominantly in the cytoplasm (FIGS. 1C, 1E, Table 1). The 273$^{his}$ mutant behaved similar to wt p53 in cellular localization (Table 1). In contrast to wt p53, mutants 143$^{ala}$, 175$^{his}$, 248$^{trp}$ and 249$^{ser}$ also exhibited only cytoplasmic localization in some cells ranging from 6 to 77% (Table 1), indicating that these mutants may have a tendency to accumulate in cytoplasm. All mutants exhibited either significantly reduced (273$^{his}$) or no ability to induce apoptosis (Table 1).

The data summarized in Table 1 indicate that an intrinsic property of wt p53 is the induction of apoptosis. Mutant 273$^{his}$ still retained wt-like activity to a small degree (subcellular localization and ability to induce apoptosis), suggesting that it is a weak mutant. While the 273$^{his}$ mutant has none of transactivating function that is important in inducing G1 growth arrest, it could still induce apoptosis, suggesting that these two events can be uncoupled. Supporting these observations are the findings that mutant 273$^{his}$ retains wt conformation as measured by PAb1620 recognition, lacks Hsp70 binding, and exhibits partial tumor suppressor activity. Other recent studies also indicate that cell cycle arrest and apoptosis may be independent outcomes following treatment with cytotoxic agents.

Mutations of the wt p53 gene result not only in loss of tumor suppressor activity but also gain of oncogenic activity. In order to demonstrate dominant negative effects of mutant p53, expression vectors encoding both wt and mutant p53 were coinjected into normal human fibroblasts as described above. The presence of the mutants, i.e., 143$^{ala}$, 175$^{his}$, 248$^{trp}$, 249$^{ser}$ or 273$^{his}$, completely abolished the induction of apoptosis by p53 (Table 1). The subcellular localization patterns of most mutants were unaltered when co-expressed with wt p53. Interestingly, we observed a lesser number of cells with only cytoplasmic staining when wt p53 was co-injected with 249$^{ser}$ (20% vs 77%), but increased percentage of cells with only cytoplasmic staining when wt p53 was co-injected with 273$^{his}$ (33% vs 0%). These data indicate that although all p53 mutants tested exhibit dominant negative effects, they may differ in their pathways to inactivate the wt p53 function. While not wishing to be bound by theory, these results are consistent with the hypothesis that regulation of apoptosis by wt p53 is an integral part of the defense mechanism against outgrowth of damaged cells which may lead to cancer development.

Example 8

Lack of Inhibition of Apoptosis with wt p53

As described herein, both wt p53 and mutant p53 (135$^{tyr}$, 249$^{ser}$ and 273$^{his}$) bind to TFIIH-associated factors, but only wt p53 inhibits the TFIIH-based DNA helicase activity contributed by XPB and XPD. Furthermore, as we demonstrate below, defects in the XPD and XPB genes particularly associated with the helicase activity result in cells resistant to p53-induced apoptosis. The cells from patient XPCS2BA contain a missense mutation at codon 99$^{phe \rightarrow ser}$ in the XPB gene, resulting in virtually complete inactivation of the NER function of the protein. (See Vermeulen, W., et al. (1994) *Am. J. Hum. Genet.* 54:191. The cells from patient XP6BE contain a defective XPD gene that also abolishes NER activity. (See Flejter, W. L., et al. (1992) *Proc. Natl. Acad. Sci U.S.A.* 89:261.) Microinjection of the wt p53 expression vector into XPCS2BA or XP6BE cells and measurement of apoptosis was carried out as described in Example 7. Results are shown in Table 2.

TABLE 2

Differential induction of apoptosis between normal primary human fibroblasts and fibroblasts from XPB and XPD patients

| Cell strains | % apoptotic cells[a] (n)[b] | p53 localization (% cells) | | |
|---|---|---|---|---|
| | | nuclei | cytoplasmic | both |
| Normal | 20(152) | 28 | 0 | 72 |
| XPCS2BA (XPB) | 4(113) | 22 | 2 | 76 |
| XP6BE (XPD) | 0(95) | 40 | 0 | 60 |

[a]Cells with the condensed and fragmented nuclei as well as the crater-like body characteristic of cells going under apoptosis.
[b]Number of p53 positive cells 24 hours following microinjection of the wild-type p53 expression vector.

Microinjection of the wt p53 expression vector into XPCS2BA or XP6BE cells resulted in expression of high levels of nuclear p53 (Table 2). The signal intensity of p53 in these cells is comparable to the levels in normal fibroblasts (C5RO) (data not shown). Although 20% of C5RO cells underwent apoptosis, only 4% of the p53-positive XPCS2BA cells and none of the XP6BE cells exhibited apoptosis at 24 hr (Table 2).

We then carried out a time-course study comparing different time points after microinjection of p53 into XPCS2BA or XP6BE cells. Cells were incubated for 6, 24, and 48 hr following microinjection of wt p53 expression vector. High levels of p53 could be detected at 6 hr following injection in all cell types although no apoptosis was observed. At 24 hr, 20% of C5RO cells, but only 4% of XPCS2BA cells had undergone apoptosis (Table 2, FIG. 2). No apoptosis was observed in XP6BE cells, as described above. At 48 hr, however, 33% of both C5RO and XPCS2BA cells and 9% of XP6BE cells had undergone apoptosis (FIG. 2). It appears that the p53 associated apoptosis is not completely abolished although a difference in timing, and possibly efficiency of apoptosis can be seen. While not wishing to be bound by theory, these differences may be due to the XPB and XPD dependent apoptosis pathways being deficient, but still marginally functioning resulted from the complex of these proteins. These differences may also reflect other signaling pathways which follow a different time course to trigger apoptosis.

In order to further demonstrate that p53 induced apoptosis in fibroblasts is mediated by effects on XPB and XPD, fibroblasts from individuals with defects in repair genes other than XPB and XPD were also examined. In particular, we infected fibroblasts from normal individuals and Xeroderma pigmentosum donors with XP-A and XP-C germline mutation by wt p53 in a retroviral expression vector under the control of CMV promoter. Infection of the p53 retroviral expression vector resulted in a moderate levels of nuclear p53 proteins expressed in all cell types tested as compared to microinjection (data not shown). The effect on apoptosis is shown in Table 3.

TABLE 3

Differential induction of apoptosis in fibroblasts from individuals with various defects in nucleotide excision repair pathway by infection of a retroviral vector encoding wt p53

| | | % apoptosis (n[b]) | |
|---|---|---|---|
| Cell Name[a] | Phenotypes | Exp I | Exp II |
| GM07532/1057 | Normal | 6.4 (204) | 11.0 (91) |
| GM00510/XP1PW | XPC | 7.1 (98) | 7.4 (244) |
| GM05509B/XP12BE | XPA | 4.5 (67) | 5.2 (155) |
| GM13025/XPCS2BA | XPB | 1.3 (78) | 0.9 (217) |
| GM10430/XP6BE | XPD | 0 (51) | 0 (168) |

[a]All cells are primary fibroblasts obtained from Coriell Institute for Medical Research between passage 10 and 15. The cell names correspond to their catalog numbers or their local user numbers that were used in the initial publications. XP-A, XP-B, XP-D, and XP-C stand for *Xeroderma pigmentosum* compleinentation group A, B, D, and C, respectively. Induction of apoptosis was achieved by infection of these cells with a retroviral vector encoding wt p53 under the control of CMV promoter, followed by an additional 48 hr incubation. The titer of viral stocks used is between 5 × 10⁴ to 1 × 10⁵ cfu/ml. Cells were fixed, stained for p53, and analyzed for apoptosis as described in Example 8, herein. Two independent experiments were performed on a separate day, and were referred to as Exp I or Exp II.
[b]n, number of p53 positive cells scored.

About 9% of GM7532 cells (normal), 5% of GM5509 cells (XPA), and 7% of GM0510 cells (XPC) consistently exhibited apoptosis (Table 3). In contrast, only 1% of XPCS2BA cells (XPB) and none of XP6BE cells (XPD) showed apoptosis (Table 3), which is consistent with the microinjection data. These results indicate that decreased sensitivity to wt p53-induced apoptosis in XP-B and XP-D cells is not due to a general overall defect in NER pathway but rather as a result of a mutation in the XPB or XPD gene.

Our results show for the first time that the association of p53 and the TFIIH (XPB/XPD) complex has functional consequence in vivo, and provide a basis for defining down-stream targets in p53 dependent apoptosis. It is already known that XPB and XPD are part of the TFIIH complex that are necessary for both basal transcription and NER. The functions of these proteins may depend on their physical association since they always form a complex in vivo. While not wishing to be bound by theory, it is possible that these three pathways have a number of steps in common using the same proteins. Furthermore, it is likely that p53 induces apoptosis by binding to and inhibiting the helicase activities of both the XPD and XPB gene products. Therefore, XP-D or XP-B cells that contain a defect only in XPD or XPB gene, respectively, are not completely resistant to the p53-induced apoptosis.

The findings that p53 inhibits DNA helicases associated with NER as well as DNA and RNA helicases involved in DNA replication and translation suggest that p53 may influence a broad range of cellular processes. Although the unwinding reaction of helicases is poorly understood, these enzymes are in fact essential for all aspects of DNA function, including DNA replication, repair, recombination, transcription, and translation. As described herein, p53 binds to XPB at a region within helicase motif III that may be essential for nucleic acid unwinding and is indispensable for its NER activity. Sequence and computer-aided secondary structure analysis of motif III from many members of the helicase superfamily indicate that they are structurally and functionally related, and could be the targets of p53. Correspondingly, p53 may act as a modulator of cellular helicase activity. It is generally believed, however, that the loss of p53 leads to genomic instability along with failure to undergo DNA damage-induced apoptosis, a defense mechanism preventing cells from surviving DNA damage that may result in the acquisition of mutations conferring uncontrolled growth advantage. Thus, while not wishing to be bound by theory, the general anti-helicase activity of p53 could be part of the signal transduction pathway associated with apoptosis upon DNA damage.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A compound comprising the amino acid sequence depicted in Seq. ID No. 2, wherein said compound (1) binds to a binding site on the XPB helicase, (2) competes with wild type p53 proteins for the binding site, and (3) inhibits the helicase activity with the proviso that the compound does not exceed 100 amino acid residues on either the amino or carboxyl terminus of SEQ ID NO:2.

2. A compound of claim 1 wherein the compound is a peptide consisting of the sequence depicted in Seq. ID No. 2.

* * * * *